(12) United States Patent
Kubota et al.

(10) Patent No.: US 7,456,017 B2
(45) Date of Patent: Nov. 25, 2008

(54) PROCESSES FOR CLONAL GROWTH OF HEPATIC PROGENITOR CELLS

(75) Inventors: Hiroshi Kubota, Chapel Hill, NC (US); Lola M. Reid, Chapel Hill, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/135,700

(22) Filed: May 1, 2002

(65) Prior Publication Data

US 2003/0032182 A1 Feb. 13, 2003

Related U.S. Application Data

(63) Continuation of application No. 09/679,663, filed on Oct. 3, 2000, now abandoned.

(60) Provisional application No. 60/157,003, filed on Oct. 1, 1999.

(51) Int. Cl.
*C12N 5/06* (2006.01)
*C12N 5/08* (2006.01)

(52) U.S. Cl. .................. 435/370; 435/373; 435/378

(58) Field of Classification Search ............ 435/370, 435/373, 384, 386, 388, 383, 352, 395, 389
See application file for complete search history.

(56) References Cited

U.S. PATENT DOCUMENTS

| 4,914,032 A | 4/1990 | Kuri-Harcuch et al. |
| 5,510,254 A | 4/1996 | Naughton et al. |
| 5,576,207 A | 11/1996 | Reid et al. |
| 5,866,420 A | 2/1999 | Talbot et al. |
| 6,242,252 B1 | 6/2001 | Reid et al. |

FOREIGN PATENT DOCUMENTS

| EP | 0 682 106 A3 | 11/1997 |
| WO | WO 93/03142 | 2/1993 |
| WO | WO 95/13697 | 5/1995 |

OTHER PUBLICATIONS

ATCC Catalogue. ATCC Cell Lines and Hybridomans. American Type Culture Collection. 8th edition. 1994. pp. 146, 516-519, 534.*
ATCC Catalogue. ATCC Cell Lines and Hybridomas. 1994. p. 522.*
Nakamura et al. "In vitro induction of neonatal rat hepatocytes by direct contact with adult rat hepatocytes". Experimental Cell Research. 1987. vol. 169, No. 1, pp. 1-14.*
Isfort et al. "The combination of epidermal growth factor and transforming growth factor-beta induces novel phenotypic changes in mouse liver stem cell lines". Journal of Cell Science, Dec. 1997, vol. 110, No. 24, pp. 3117-3129.*
Kohno et al. Virchows Arch B Cell Pathol Incl Mol Pathol. 1993; 63 (5):317-24.*
Y. Zhai and S. Knechtle Two Distinct Forms of Soluble MHC Class I Molecules Synthesized by Different Mechanisms in Normal Rat Cells In Vitro, *Human Immunology*, 59, p. 404-414, Elsevier Science, Inc.
H. Bisgaard et al. Modulation of the Gene NetworkConnected to Interferon-y in Liver Regeneration from Oval Cells, *American Journal of Pathology*, vol. 155, No. 4 Oct. 1999, p. 1075-1085, American Society for Investigating Pathology.
L. Rogler Selective Biopotential Differentiation of Mouse Embryonic Hepatoblasts in Vitro, *American Journal of Pathology*, vol. 150, No. 2 Feb. 1997, p. 591-602 American Society for Investigating Pathology.
H. Kubota and L. Reid Clonogenic Hepatoblasts Common Precursors for Haptocytic and Biliary Lineages, Are Lacking Classical Major Histocompatibility Complex Class I Antigen, *PNAS*, vol. 97, No. 22, Oct. 24, 2000, p. 12132-12137.
Limiat A. et al. Comparative Analysis of Surface Antigens in Cultured Human Outer Root Sheath Cells and Epidermal Keratinocytes: Persistence of Low Expression of Class I MHC Antigens in Outer Root Sheath Cells in vitro; *British Journal of Dermatology*, 1994, 131, 184-190.
Tateno, C. et al. Growth Potential and Differentiation Capacity of Adult Rat Hepatocytes in vitro; *Wound Repair and Regeneration*, vol. 7, No. 1, Jan.-Feb. 1999, p. 36-43.
Haque, S. et al. Identification of Bipotential Progenitor Cells in Human Liver Regeneration; *Laboratory Investigation*, vol. 75, No. 5 p. 699-705, 1996.
Haruma, Y. et al. Identification of Bipotential Progenitor Cells in Human Liver Development, *Hepatology*, vol. 23, No. 3, Mar. 1996, p. 476-481.
Seglen, Per O., "Preparation of Isolated Rat Liver Cells," Methods in Cell Biology , pp. 29-83 (1976) Academic Press.

* cited by examiner

*Primary Examiner*—Vera Afremova
(74) *Attorney, Agent, or Firm*—Gilberto M. Villacorta; Sunit Talapatra; Foley & Lardner LLP

(57) ABSTRACT

A method of propagating mammalian endodermally derived progenitors such as hepatic progenitors, their progeny, or mixtures thereof is developed which includes culturing mammalian progenitors, their progeny, or mixtures thereof on a layer of embryonic mammalian feeder cells in a culture medium. The culture medium can be supplemented with one or more hormones and other growth agents. These hormones and other growth agents can include insulin, dexamethasone, transferrin, nicotinamide, serum albumin, β-mercaptoethanol, free fatty acid, glutamine, $CuSO_4$, and $H_2SeO_3$. The culture medium can also include antibiotics. Importantly, the culture medium does not include serum.

The invention includes means of inducing the differentiation of the progenitors to their adult fates such as the differentiation of hepatic progenitor cells to hepatocytes or biliary cells by adding, or excluding epidermal growth factor, respectively.

The method of producing mammalian progenitors is useful in that the progenitors can be used subsequently in one or more of the following processes: identification of growth and differentiation factors, toxicological studies, drug development, antimicrobial studies, or the preparation of an extracorporeal organ such as a bioartificial liver.

36 Claims, 15 Drawing Sheets

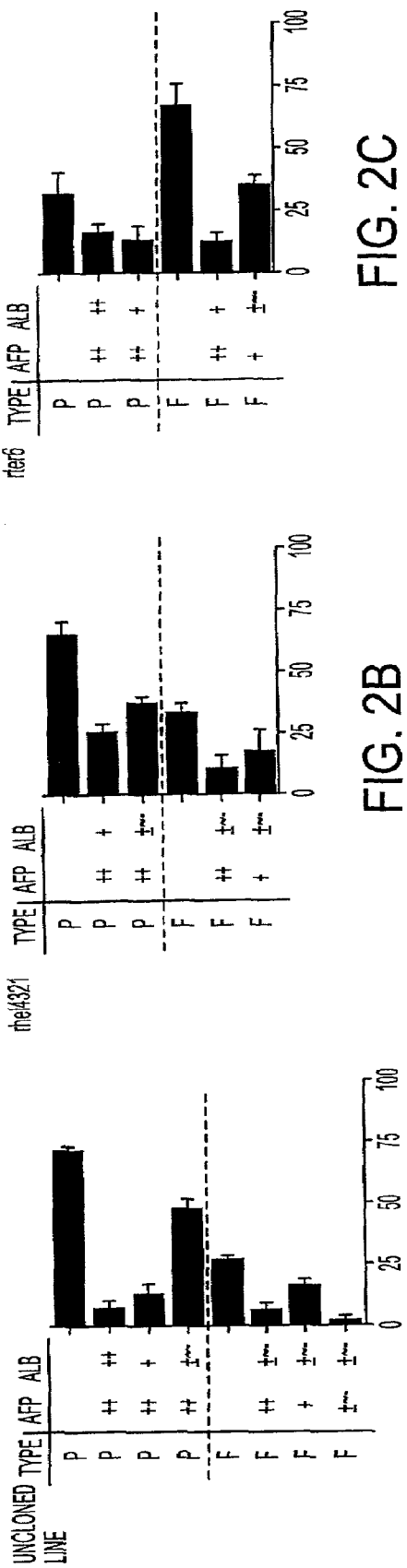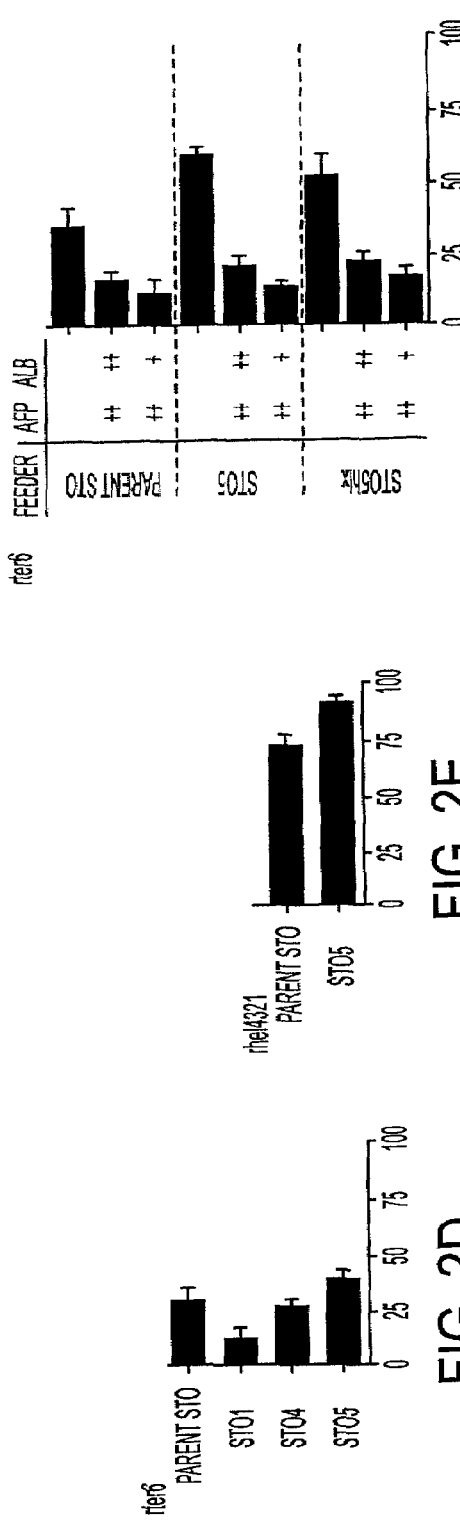

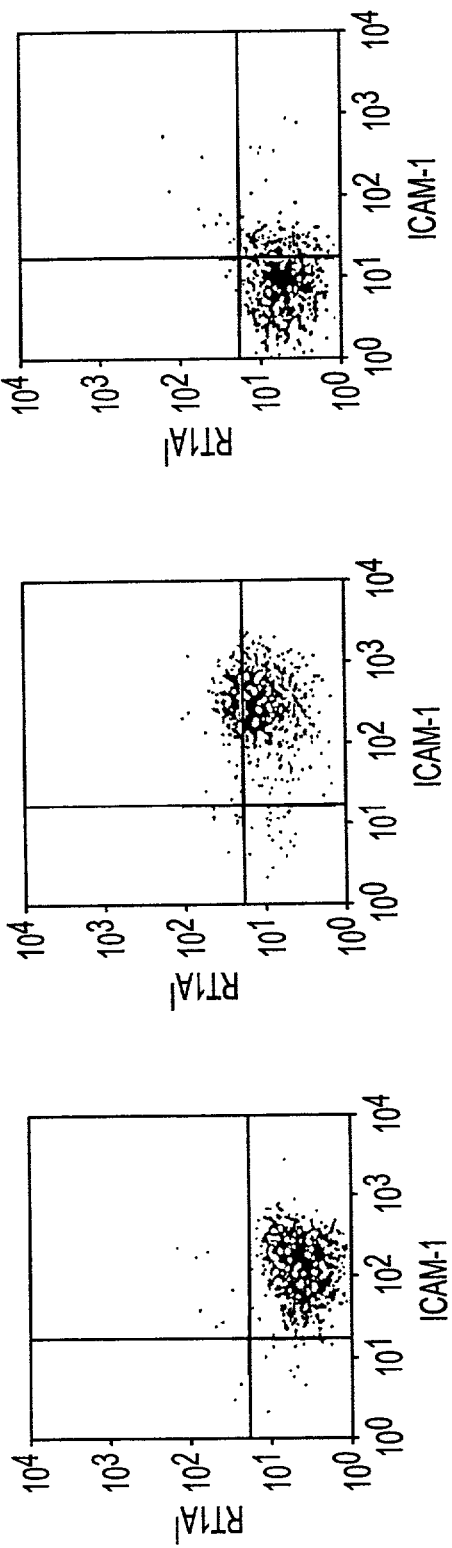
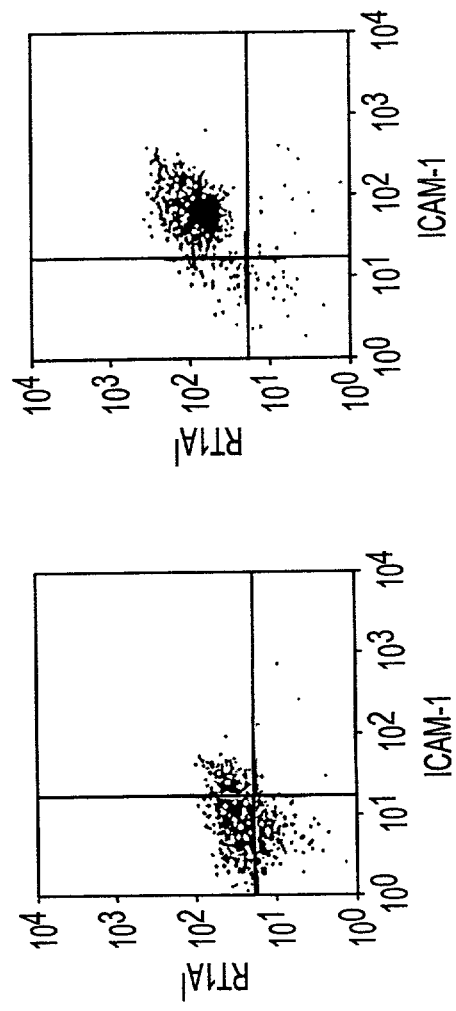
FIG. 4B-1
FIG. 4B-2
FIG. 4B-3
FIG. 4B-4
FIG. 4B-5

PROCESSES FOR CLONAL GROWTH OF HEPATIC PROGENITOR CELLS

This application is a continuation of U.S. application Ser. No. 09/679,663 filed on Oct. 3, 2000 now abandoned which claims priority from U.S. Provisional Application No. 60/157,003 filed on Oct. 1, 1999 and is incorporated by reference herein.

1. FIELD OF THE INVENTION

The present invention relates to novel conditions for clonal growth of mammalian hepatic progenitors, including pluripotent cells, stem cells, and other early hepatic progenitor cells. In particular, the invention relates to methods of propagating hepatic progenitor cells using defined culture medium and feeder cells in co-cultures. Moreover, the invention relates to the cells used as feeders and capable of sustaining hepatic progenitor cell growth.

2. DESCRIPTION OF RELATED ART

Identification of multipotential progenitor cell populations in mammalian tissues is important both for clinical and commercial interests and also for understandings of developmental processes and tissue homeostasis. Progenitor cell populations are ideal targets for gene therapy, cell transplantation and for tissue engineering of bioartificial organs (Millar, A D. 1992 Nature 357, 455; Langer, R. and Vacanti, J. P. 1993 Science 260, 920; Gage, F. H. 1998 Nature 392, 18).

The existence of tissue-specific, "determined" stem cells or progenitors having high growth potential and/or pluripotentiality is readily apparent from studies on hematopoictic stem cells (Spangrude, G. J. et al. 1988 Science 241, 58), neuronal stem cells (Davis, A. A., and Temple, S. 1994 Nature 372, 263; Stemple, D. L., and Anderson, D. J. 1992 Cell 71, 973) and epidermal stem cells (Jones, P. H. and Watt, F. M. 1993 Cell 73, 713), each having been identified clonally by using the particular methods appropriate for that tissue. These progenitors are regarded as the cells responsible for normal hematopoietic, neuronal or epidermal tissue homeostasis and for regenerative responses after severe injury (Hall, P. A., and Watt, F. M. 1989 Development 106, 619).

The mammalian adult liver has a tremendous capacity to recover after either extensive hepatotoxic injury or partial hepatectomy (Fishback, F. C. 1929 Arch. Pathol. 7, 955); (Higgins, G. M. and Anderson, R. M. 1931 Arch. Pathol. 12, 186), even though the liver is usually a quiescent tissue without rapid turnover. Data from recent studies in the mouse have been interpreted to suggest that adult parenchymal cells have an almost unlimited growth potentiality as assayed by serial transplantation experiments (Overturf et al. 1997 Am. J Pathol. 151, 1273); (Rhim, J. A. et al. 1994 Science 263, 1149). These experiments made use of heterogeneous liver cell populations limiting the ability to prove that the growth potential observed derived from adult parenchymal cells, from a subpopulation of adult parenchymal cells and/or from immature stages of the parenchymal cells (i.e. progenitors). Furthermore, the studies show no evidence for biliary epithelial differentiation, since the hosts used had either albumin-urokinase transgenes or, in the other case, a tyrosine catabolic enzyme deficiency; both types of hosts have conditions that selected for the hepatocytic lineage. Therefore, the assay was incapable of testing for bipotent cell populations.

Several histological studies establish that early hepatic cells from midgestational fetuses have a developmental bipotentiality to differentiate to bile duct epithelium as well as to mature hepatocytes (Shiojiri, N. 1997 Microscopy Res. Tech. 39, 328-35). Hepatic development begins in the ventral foregut endoderm immediately after the endodermal epithelium interacts with the cardiogenic mesoderm (Douarin, N. M. 1975 Medical Biol. 53, 427); (Houssaint, E. 1980 Cell Differ. 9, 269). This hepatic commitment occurs at embryonic day (E) 8 in the mouse. The initial phase of hepatic development becomes evident with the induction of serum albumin and alpha-fetoprotein mRNAs in the endoderm and prior to morphological changes (Gualdi, R. et al. 1996 Genes Dev. 10, 1670). At E 9.5 of mouse gestation, the specified cells then proliferate and penetrate into the mesenchyme of the septum transversum with a cord-like fashion, forming the liver anlage. Although the liver mass then increases dramatically, the increase in mass is due largely to hematopoietic cells, which colonize the fetal liver at E10 in the mouse (Houssaint, E. 1981 Cell Differ. 10, 243) and influence the hepatic cells to show an extremely distorted and irregular shape (Luzzatto, A. C. 1981 Cell Tissue Res. 215, 133). Interestingly, recent data from gene-targeting mutant mice indicates that impairment of a number of genes has led to lethal hepatic failure, apoptosis and/or necrosis of parenchymal cells between E12 to E15 (Gunes, C. et al. 1998 EMBO J. 17, 2846); (Hilberg, F. et al. 1993 Nature 365, 1791); (Motoyama, J. et al. 1997 Mech. Dev. 66, 27); (Schmidt, C. et al. 1995 Nature 373, 699). Especially gene disruptions that are part of the stress-activated cascade (Ganiatsas, S. et al. 1998 Proc. Natl. Acad. Sci. USA 95, 6881); (Nishina, H. et al. 1999 Development 126, 505) or anti-apoptotic cascade (Beg, A. et al. 1995 Nature 376, 167); (Li, Q. et al. 1999 Science 284, 321); (Tanaka, M. et al. 1999. Immunity 10, 421) can result in severely impaired hepatogenesis, not hematopoiesis, in spite of the broad expression of the inactivated gene. It isn't clear whether hepatic cells are intrinsically sensitive to developmental stress stimuli or that the particular microenvironment in fetal liver per se causes such destructive effects (Doi, T. S. et al 1999 Proc. Natl. Acad. Sci. USA 96, 2994). On the other hand, the basic architecture of adult liver is dependent on the appearance of the initial cylinder of bile duct epithelium surrounding the portal vein (Shiojiri, N. 1997 Microscopy Res. Tech. 39, 328). Immunohistologically, the first sign of the differentiation of intrahepatic bile duct epithelial cells is the expression of biliary-specific cytokeratin (CK). CK proteins, the cytoplasmic intermediate filament (IF) proteins of epithelial cells, are encoded by a multigene family and expressed in a tissue- and differentiation-specific manner (Moll, R. et al. 1982 Cell 31, 11). CK19 is one of the most remarkable biliary markers, because adult hepatocytes don't express CK19 at all, whereas adult biliary epithelial cells do express this protein. Only CK8 and CK18 are expressed through early hepatic cells to adult hepatocytes (Moll, R. et al. Cell 1982, 31, 11. At El 5.5 in the rat development, corresponding to E14 in the mouse, the biliary precursors are heavily stained by both CK18 and CK8 antibodies, and some biliary precursors express CK19. As development progresses, maturing bile ducts gradually express CK7 in addition to CK19 and lose the expression of ALB (Shiojiri, N. et al. Cancer Res. 1991, 51, 2611). Although hepatic cells as early as E13 in the rat are thought to be a homogeneous population, it remains to be seen whether all early hepatic cells can differentiate to biliary epithelial cell lineage, and how their fates are determined. Definitive lineage-marking studies, such as those using retroviral vectors, have not been done for hepatic cells, and clonal culture conditions requisite for the demonstration of any bipotent hepatic progenitor cells have not been identified.

For clonal growth analyses, one major obstacle is the explosive expansion of hematopoietic cells, marring the ability to observe ex vivo expansion of hepatic cells. Therefore an enrichment process for the hepatic population must be used. Although the surface markers needed to fractionate the hematopoietic cells in fetal liver have been investigated in detail (Dzierzak, E. et al. *Immunol. Today* 1998, 19, 228), those for hepatic progenitor cells are still poorly defined, since the studies are in their infancy (Sigal, S. et al. *Hepatology* 1994,19, 999). Furthermore, the ex vivo proliferation conditions typically used for adult liver cells result in their dedifferentiation with loss of tissue-specific functions such as ALB expression (Block, G. D. et al. *J. Cell Biol.* 1996, 132, 1133). A somewhat improved ability to synthesize tissue-specific mRNAs and a restoration in the ability to regulate tissue-specific genes fully post-transcriptionally occurs only in liver cells maintained in the absence of serum and with a defined mixture of hormones, growth factors and/or with certain extracellular matrix components (Jefferson, D. M. et al. *Mol. Cell. Biol.* 1984, 4, 1929; Enat, R. et al Proc. Natl. Acad. Sci., 1984, 81, 1411). Proliferating fetal hepatic cells, however, maintain the expression of such serum proteins in vivo. What has not been clear in the field is how to maintain and grow hepatic progenitors in vitro. There is an unfilled need for identification of conditions that sustain the ex vivo expansion of hepatic progenitor cells. Likewise there is an unfilled need for an in vitro colony forming assay (CFA) for defining clonal growth potential of hepatic progenitors freshly isolated from liver tissue; clonal growth is defined as the ability of a single cell seeded into culture being able to generate a population of daughter cells that are clonally derived from the seeded cell. Others have described colony growth (Block, G. D. et al. *J. Cell Biol.* 1996, 132, 1133), consisting of aggregates of cells growing closely together in liver cultures seeded at high cell densities; however, the colonies of cells described in these prior studies could not be subcultured and, therefore, by definition were not clonal and of limited utility.

Others have attempted to grow hepatocytes in vitro. U.S. Pat. No. 5,510,254 to Naughton et al. claims the culture of hepatocytes depends on a three-dimensional framework of biocompatible but non-living material. There is an unfilled need for hepatocyte culture conditions where no artificial framework is necessary and that provides the condition for hepatic progenitors to be expanded and cultured. Furthermore, there is a need for cloned hepatic progenitors with bipotential differentiation capability, that is ability to generate both biliary and hepatocytic lineages, and suitability for use as components of a bioartificial liver, for testing of hepatotoxins and drug development, among other uses.

U.S. Pat. No. 5,559,022 to Naughton et al., claims liver reserve cells that bind Eosin Y, a stain that was used to characterize the "reserve cells", but did not use well-established markers for liver cells, nor provided methods for clonal expansion, nor provided markers by which to isolate viable liver reserve cells. There is an unfilled need for methods that teach how to isolate and culture cells that have many features essential to hepatic progenitors, including expression of at least one specific marker and the potential to differentiate into either hepatocytes or biliary cells. There is also an unfilled need for methods for clonal growth of hepatic progenitors. Clonal growth is essential as a clear and rigorous distinction and identification of pluripotent hepatic progenitors.

U.S. Pat. No. 5,405,772 to Ponting claims a culture medium for cell growth. The U.S. Pat. No. 5,405,772 requires the use of 3-30 µg/ml cholesterol, 5-30 µg/ml nucleosides, and either 2-100 µg/cm$^2$ collagen IV or 0.5-100 µg/cm$^2$ fibronectin. There is a need for a culture medium that is specific for, and optimized for, hepatic progenitor cell growth.

U.S. Pat. No. 4,914,032 to Kuri-Harcuch et al. claims a process for culturing hepatocytes. In contrast to the instant invention, U.S. Pat. No. 4,914,032 fails to teach either the culture of hepatic progenitors or clonal growth conditions for hepatic cells. Likewise, U.S. Pat. No. 5,030,105 to Kuri-Harcuch et al. claims methods of assessing agents by treating hepatocyte cultures. There is an unfilled need for clonal growth conditions so that defined populations of cells may be used for testing and also for methods for the culture of hepatic progenitors.

The U.S. Pat. No. 5,858,721 to Naughton et al. claims transfection of stromal cells. The U.S. Pat. No. 5,858,721 patent is limited, however, by the requirement for a framework of biocompatible, non-living material. The instant invention by contrast, there is an unfilled need for growth conditions that do not require a synthetic meshwork.

The present inventors have recognized the inadequacy of growing mature liver cells, such as hepatocytes, rather than the far more useful hepatic progenitors. They have carefully defined the isolation parameters for hepatic progenitors and requirements for clonal growth. The progenitor cells and the methods for selecting and culturing the progenitors have many uses, including utility in medicine for treatment of patients with liver failure, and utility for evaluation of toxicity agents, and utility for evaluation of drugs.

U.S. Pat. Nos. 5,576,207 and 5,789,246 to Reid, et al. teach the need for feeders and a hormone-supplemented defined medium. These prior studies advocated use of embryonic liver stromal cells in combination with defined extracellular matrix substrata, and a serum-free, hormonally defined medium as conditions for expansion of hepatic progenitors. However, the defined medium used was more complex than the one used by the instant invention; the cells were plated onto purified matrix substrata (type IV collagen and laminin), whereas here they are plated directly onto the feeders (that supply that matrix); and the embryonic stromal cells were prepared as primary cultures of embryonic livers and were not established as cell lines. By use of embryonic stromal cell lines, the feeder cells are provided by a far easier, more practical and more reproducible means of supporting the cells. Moreover, it is reasonable to assume that the STO feeders will not restrict support to just hepatic progenitors but can be used for progenitors from multiple tissue types. The prior patent, the hepatic progenitor cultures were seeded at high cell densities and expansion of them was observed as colony formation, meaning that the aggregates of the cells, not clones of cells, were induced to proliferate.

3. SUMMARY OF THE INVENTION

The present invention relates to a method of propagating progenitors, their progeny, or mixtures thereof. In particular, the present invention relates to a method of propagating endodermally-derived progenitors, their progeny, or mixtures thereof. The cells are derived from endodermal tissue. Then the endodermally-derived progenitors, their progeny, or mixtures thereof, are cultured on a layer comprising feeder cells in a culture medium. The progenitors, their progeny, or mixtures thereof, can be vertebrate cells. The progenitors, their progeny, or mixtures thereof, can express the phenotype ICAM or ICAM-1 positive and classical MHC class I antigen negative. The classical MCH class I antigen is also termed MHC class Ia antigen.

The present invention also relates to a method of culturing hepatic stem and other progenitor cells using a serum-free, hormone-supplemented, defined medium and feeder cells. Also, the invention relates to a method of culturing the progeny of progenitor cells, or combinations of progenitor cells and progenitor progeny. Preferably, the progenitor cells are hepatic progenitors. Likewise, the present invention relates to a method of cloning hepatic pluripotent progenitor cells using specific culture conditions. Preferably, the invention relates to a method of cloning hepatic pluripotent progenitor cells. The hepatic pluripotent progenitor cells may be derived from any invertebrate or vertebrate species and more preferably mammalian. Even more preferably, the hepatic pluripotent progenitor cells are human, primate, pig, dog, rat, rabbit or mouse in origin. Most preferably the pluripotent progenitor cells are human in origin. The invention teaches particular culture conditions that are required for the ex vivo expansion of hepatic progenitor cells, and their progeny. The invention also teaches use of embryonic feeder cells, such as STO mouse embryonic cells, as feeder cells for hepatic progenitors. The feeder cells are used in combination with a novel serum-free, hormonally defined medium (HDM) taught in the invention. The combination enabled the inventors to establish various rat fetal hepatic cell lines from E15 rat livers without malignant transformation of the cells.

Furthermore, the invention relates to methods of cloning feeder cells capable of sustaining propagation of hepatic progenitor cells, and their progeny.

The invention also relates to specific cell lines that, when used as feeders, support hepatic progenitor cell growth.

The invention additionally relates to methods of cloning hepatic progenitor cells. The invention teaches the use of the hepatic cell lines and the HDM-STO co-culture system for development of an in vitro colony forming assay (CFA) for defining clonal growth potential of freshly isolated hepatic progenitors. The CFA, when combined with cells purified by specific antigenic profile, reveals bipotent hepatic progenitors. For example, progenitors from E13 rat livers, corresponding to E11.5 in the mouse, and with high growth potential have the same phenotype as classical MHC class I $(RT1A^1)^-$, OX18 (pan-MHC class I)$^{dull}$, and intracellular adhesion molecule 1 (ICAM-1)$^+$.

The invention additionally relates to the culture medium capable of sustaining clonal hepatic cell growth. The culture medium features several specific hormones and nutrients and an absence of serum.

Further still, the invention relates to the culture of heptic progenitors in medium with feeder cell biosynthetic products.

The invention further relates to methods of inducing hepatic cell differentiation, including production of hepatocyte and biliary cell phenotypes. Epidermal growth factor (EGF) is taught in this invention to influence both growth of the progenitor colonies and their fates as either hepatocytes or biliary epithelial cells.

4. BRIEF DESCRIPTION OF THE DRAWINGS

5. DETAILED DESCRIPTION OF THE PREFERRED EMBODIMENTS

Figure 1A:
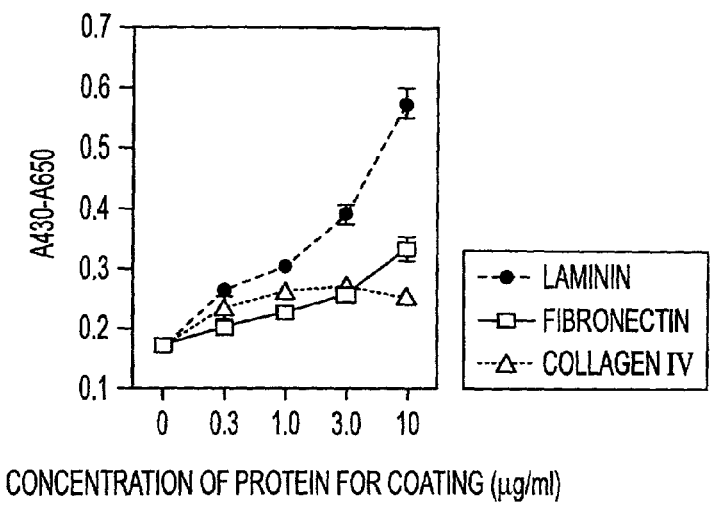
FIG. 1 is a characterization of hepatic cell lines from day 15 fetal rat liver.

The instant invention is a process for propagation and use of stem cells. Various tissues are appropriate sources of progenitors, including tissues of ectoderm, mesoderm and endoderm origin. The ectoderm tissues can include skin tissue, brain tissue and other nerve tissue. The mesoderm tissues can include muscle, the blood and hemopoietic systems. The endoderm tissues can include the gut, stomach, pancreas thyroid and glands associated with the digestive system. In particular, the instant invention is a process for the propagation of hepatic stem cells and of other hepatic progenitor cells. The process involves exposing populations of isolated hepatic stem cells and/or hepatic progenitor cells and/or their progeny, to growth conditions capable of sustaining clonal growth, that is, growth at very low cell densities. In a preferred embodiment, the process involves using a serum-free, hormone-supplemented, defined medium to support the propagation of hepatic progenitor cells on a layer of feeder cells. The function of the feeder cells is multi-fold, including supplying nutrients, supplying an attachment surface, and secreting into the medium certain growth factors and extracellular matrix components needed for survival, growth and/ or differentiation of the hepatic progenitor cells. In another preferred embodiment, the process involves selecting for cells that are capable of sustaining the growth of hepatic stem and hepatic progenitor cells. The feeder cells may be from reptiles, birds, crustaceans, fish, annelids, molluscs, nematodes, insects, or mammals, preferably human. Preferably, the feeder cells derive from embryonic tissues. Also, preferably, the feeder cells derive from embryonic tissue. Also, preferably, the feeder cells can derive from embryonic liver tissue. Additionally, the feeder cells may be genetically modified. In a still more preferred embodiment, the process involves cloning feeder cells that optimally sustain hepatic cells.

Any method of isolating hepatic stem and hepatic progenitor cells is acceptable, including by affinity-based interactions, e.g. affinity panning, immunosurgery in combination with complement, by flow cytometry, by centrifugal elutriation, by differential centrifugation, etc. The isolated hepatic stem and progenitor cells, have the capacity to express some or all of the phenotype markers (classical MHC class I$^-$, ICAM-1$^+$, OX18$^{dull}$, alpha-fetoprotein$^+$, or albumin$^+$). It is another embodiment of the invention that the hepatic progenitors express a growth pattern in the colonies characterized by formation of piled-up cells as aggregates, colonies or clusters.

It is a preferred embodiment of the instant invention that hepatic cells be selectively grown in a serum-free, hormone-supplemented, defined medium (HDM).

The composition of HDM comprises a nutrient medium including, but not limited to a mixture of Dulbecco's modified Eagle's medium and Ham's F12 to which is added up to about 40 ng/ml EGF, up to about 5-10 µg/ml insulin, up to about $10^{-6}$ M Dexamethasone or other glucocorticoid hormone, up to about 10 µg/ml iron-saturated transferrin, up to about $5 \times 10^{-2}$ M nicotinamide, up to about 2% bovine serum albumin, up to about $5 \times 10^{-4}$ M 2-mercaptoethanol or equivalent reducing agent, up to about 8 µeq/l free fatty acid, up to about $2 \times 10^{-2}$ M glutamine, up to about $1 \times 10^{-6}$ M CuSO$_4$, up to about $3 \times 10^{-8}$ M H$_2$SeO$_3$ and, optionally, antibiotics. Antibiotics can include penicillin, streptomycin, gentamycin, and others common in the art, and combinations thereof. One skilled in the art will know that other nutrient media, e.g. Ham's F-10, Medium 199, or one of the MCDB series including MCDB 151 and MCDB 302, can, after minimal testing, be used in place of DMEM/F12. The most minimal conditions for cell expansion are use of the feeders in the absence of any hormones; and the most critical of the hormonal requirements listed above are glucocorticoids, insulin, transferrin, and EGF constituting the strict hormonal mitogens for progenitor cell expansion. Other hormonal factors can be added and might have secondary growth effects but do not replace the critical requirements noted above. Likewise, changes in the hormone constituents such as can be made by one of ordinary skill in the art, are within the scope of the instant invention.

Preferable ranges include 10-50 ng/ml EGF, 2-10 ug/ml insulin, $5\times10^{-7}$M to $5\times10^{-6}$ M dexamethasone (9α-fluoro-16α-methyl-prednisolone), 5-20 ug/ml iron-saturated transferrin, $2$-$8\times10^{-3}$M nicotinamide, 0.05-0.5% serum albumin, $2$-$8\times10^{-5}$ M 2-mercaptoethanol, 5-10 ueq free fatty acid mixture, $1$-$3\times10^{-3}$ M glutamine, $0.5$-$2\times10^{-6}$ M $CuSO_4$, $1$-$5\times10^{-8}$M $H_2SeO_3$, 1-5 uM palmitic acid, 0.1-0.4 uM palmitoleic acid, 0.5-1.2 uM stearic acid, 0.5-2 uM oleic acid, 1-5 uM linoleic acid, and 0.2-0.8 uM linolenic acid.

The serum-free, hormonally defined culture medium of the invention, is suitable for the clonal growth of hepatic cells. This HDM contains a basal medium that can be any of a number of options such as Dulbecco's modified Eagle's medium (DME), Ham's F12, RPMI1640, Williams E medium, etc. A preferred embodiment is a 1:1 mixture of Dulbecco's modified Eagle's medium and Ham's F12 (DMEM/F12, from, for example GIBCO/BRL, Grand Island, N.Y.). The basal medium is supplemented with epidermal growth factor, EGF (from, for example, Collaborative Biomedical Products) at a preferred concentration of 10 ng/ml, insulin (from, for example, Sigma) at a preferred concentration of 5 μg/ml, $10^{-6}$M Dexamethasone (from, for example, Sigma), 10 μg/ml iron-saturated transferrin (Sigma), $4.4\times10^{-3}$M nicotinamide (from, for example, Sigma), 0.2% serum albumin (from, for example, Sigma), $5\times10^{-5}$M 2-mercaptoethanol (from, for example, Sigma), 7.6 μeq/1 free fatty acid mixture (2.4 uM palmitic acid, 0.21 uM palmitoleic acid, 0.88 uM stearic acid, 1 uM oleic acid, 2.7 uM linoleic acid, and 0.43 uM linolenic acid), $2\times10^{-3}$M glutamine (from, for example, GIBCO/BRL), $1\times10^{-6}$M $CuSO_4$, $3\times10^{-8}$M $H_2SeO_3$ and antibiotics. The growth factors secreted by the feeder cells, including but not limited to insulin-like growth factors (IGFs), interleukin (IL)-6 family, hepatocyte growth factors (HGFs), and fibroblast growth factors (FGFs), can be added to the culture medium to augment feeder effects but have not been found to replace feeder effects when added singly or in various combinations, meaning that the feeder cells are producing other signals, yet unidentified that are needed alone or in combination with these growth factors.

It is a still further embodiment of the invention that the hepatic progenitor cells are propagated from a single progenitor cell, that is, that the cells are cloned. Growing cells in colonies does not necessarily equate with clonal growth which implicitly and explicitly is defined as propagation of cells derived from a single cell. Any of several methods of cloning known in the art are suitable, including diluting the progenitor cells to one cell, or less, per cell culture plate well, a method termed limiting dilution. Similarly progenitor cells may be cloned with the use of cloning rings, by selective ablation, by dilute culture on microparticles, by single-cell sorting using flow cytometry, by picking individual cells with micropipet or optical tweezers, and by agar.

It is a yet further embodiment of the invention that many of the cloned progenitor cells are capable of mitosis. It is preferred that the progenitor cells are capable of a least one cycle of mitosis and even more preferred that the progenitor cells are capable of at least ten cycles of division.

It is a still yet further embodiment of the invention that hepatic progenitor cells and their progeny are propagated in medium supplemented with metabolic and biosynthetic products of feeder cells. The supplement can take the form of conditioned medium, that is, medium previously incubated with living feeder cells. Preferably the supplementing can take the form of isolating from feeder cell-conditioned medium those factors including proteins, peptides, lipids, carbohydrates, and metabolic regulators that sustain and enhance the growth of hepatic progenitors and their progeny. The proteins can include soluble and insoluble components of extracellular matrix and growth factors including epidermal growth factor and insulin-like growth factors.

It is further preferred that hepatic cells be selectively grown in culture using a layer of feeder cells, where those feeder cells are embryonic or adult cells or other suitable cells. In one embodiment the feeder cells are stromal cells or fibroblasts. The fibroblasts or other suitable cells may be genetically modified, e.g. by transfection. It is preferred that the fibroblasts or other suitable cells be human, non-human primate, pig, dog, rabbit, rat, or mouse mesodermal cells, and other mammalian and avian mesodermal cells are also suitable. Furthermore, the fibroblasts can be cloned and selected for the ability to support hepatic progenitor cells.

It is a preferred embodiment of the instant invention that isolated hepatic progenitor cells be committed to a hepatocyte or biliary cell lineage by the selective application, or absence, of epidermal growth factor (EGF), or other differentiation signal.

It is a still more preferred embodiment of the instant invention that isolated stem cells and other hepatic progenitor cells be used as a component of a bioartificial liver that can be used as an extracorporeal liver assist device. It is a still more preferred embodiment of the instant invention that the bioartificial liver containing isolated hepatic progenitor cells and their progeny be used to support the life of a patient suffering from liver malfunction or failure.

6. EXAMPLES

The following examples are illustrative of the invention, but the invention is by no means limited to these specific examples. The person of ordinary skill in the art will find in these examples the means to implement the instant invention. The person of ordinary skill in the art will recognize a multitude of alternate embodiments that fall within the scope of the present invention.

6.1. Preparation and Analysis of Hepatic Stem and Hepatic Progenitor Cells

Rats. Pregnant Fisher 344 rats are obtained from Charles River Breeding Laboratory (Wilmington, Mass.). For timed pregnancies, animals are put together in the afternoon, and the morning on which the plug is observed is designated day 0. Male Fisher 344 rats (200-250g) are used for adult liver cells.

Establishment of hepatic cell lines. Fetal livers are prepared from day 15 of the gestation. Single cell suspensions are obtained by incubating the livers with 0.05% trypsin and 0.5 mM EDTA or 10 units/ml thermolysin (Sigma, St. Louis, Mo.) and 100 units/ml deoxyribonuclease I (Sigma) for at 37° C. The cells are overlayed on Ficoll-paque (Pharmacia Biotech, Uppsala, Sweden) for gradient density centrifugation at 450 g for 15 min. The cells from the bottom fraction are inoculated into tissue culture dishes coated with 17 mg/ml collagen type IV (Collaborative Biomedical Products, Bedford, Mass.) or 12 μg/ml laminin (Collaborative Biomedical Products) for th1120-3 and rter6 or rhe14321, respectively. The serum-free hormonally defined culture medium, HDM, is a 1:1 mixture of Dulbecco's modified Eagle's medium and Ham's F12 (DMEM/F12, GIBCO/BRL, Grand Island, N.Y.), to which is added 20 ng/ml EGF (Collaborative Biomedical Products), 5 µg/ml insulin (Sigma), $10^{-7}$M Dexamethasone (Sigma), 10 µg/ml iron-saturated transferrin (Sigma), $4.4\times 10^{-3}$M nicotinamide (Sigma), 0.2% Bovine Serum Albumin (Sigma), $5\times 10^{-5}$M 2-mercaptoethanol (Sigma), 7.6 µeq/l free fatty acid, $2\times 10^{-3}$M glutamine (GIBCO/BRL), $1\times 10^{-6}$M $CuSO_4$, $3\times 10^{-8}$M $H_2SeO_3$ and antibiotics. Each concentration given is the final concentration in the medium. After 4 weeks of culture, trypsinized cells are cultured on a feeder layer of mitomycin C-treated STO mouse embryonic fibroblast line (American Type Culture Collection, Rockville Md.). Th1120-3, rter6, and rhe14321 are cloned from three independent preparations of fetal hepatic cells and are maintained on STO feeder cells with HDM. After the establishment of the cell lines, the concentration of EGF is reduced to 10 ng/ml for all cell cultures.

Cell adhesion assay. Adhesion of cells to fibronectin (Collaborative Biomedical Products), laminin and collagen type IV is evaluated using 96 well micro-titer plates (Corning, Cambridge, Mass.) coated with these proteins at 0.3 to 10 µg/ml. After removing the STO cells by Percoll (Pharmacia Biotech) gradient density centrifugation at 200 g for 15 min, $3\times 10^4$ cells of the hepatic cell lines, th1120-3, rter6, and rhe14321, are cultured in each well for 10 hours with HDM. After rinsing twice to remove floating cells, fresh medium with the tetrazolium salt WST-1 (Boehringer Mannheim, Indianapolis, Ind.) is added to measure the number of variable adherent cells. After 4 hours, the absorbance is determined according to the manufacturer's protocol.

STO Sublines. One hundred cells of parent STO from ATCC are cultured in 100 mm culture dishes for 7 days in DMEM/F12 supplemented with 10% heat-inactivated fetal bovine serum, $2\times 10^{-3}$M glutamine, $5\times 10^{-5}$M 2-mercaptoethanol and antibiotics. Four subclones are selected for further characterization according to the cell morphology and the growth speed. Although CFA for rter6 is performed in the four subclones, one of them, STO6, does not persist in attaching to culture plates after mitomycin C-treatment. One subclone, STO5, is transfected with pEF-Hlx-MC1neo or pEF-MC1neo kindly provided from Dr. J. M. Adams, The Walter and Eliza Hall Institute of Medical Research. Linearized plasmids at Nde I site are introduced into cells by DOSPER liposomal transfection reagent (Boehringer Mannheim). After G418 selection, six clones are isolated. Three clones of each are analyzed by CFA.

Immunohistochemical Staining of Colonies. Culture plates are fixed in methanol-acetone (1:1) for 2 min at room temperature, rinsed and blocked by Hanks Balanced Salt Solution (HBSS) with 20% goat serum (GIBCO/BRL) at 4° C. For double immunohistochemistry of alpha-fetoprotein and albumin, plates are incubated with anti-rat albumin antibody (ICN Biomedicals, Costa Mesa, Calif.) followed by Texas Red-conjugated anti-rabbit IgG (Vector laboratories, Burlingame, Calif.) and FITC-conjugated anti rat alpha-fetoprotein polyclonal antibody (Nordic Immunology, Tilburg, Netherlands). For double labeling of albumin and CK19, anti-CK19 monoclonal antibody (Amersham, Buckinghamshire, England) and FITC-conjugated anti mouse IgG (Caltag, Burlingame, Calif.) are used instead of anti alpha-fetoprotein antibody.

Dissociation of E13 of fetal liver. Fetal livers are dissected into ice-cold $Ca^{++}$ free HBSS with 10 mM HEPES, 0.8 mM $MgSO_4$ and 1 mM EGTA (pH7.4). The livers are triturated with 0.2% type IV collagenase (Sigma) and 16.5 units/ml thermolysin (Sigma) in HBSS prepared with 10 mM HEPES, 0.8 mM $MgSO_4$, and 1 mM $CaCl_2$. After incubation at 37° C. for 10 min, the cell suspension is digested with 0.025% trypsin and 2.5 mM EDTA (Sigma) for 10 min. Trypsin is then quenched by addition of 1 mg/ml trypsin inhibitor (Sigma). Finally, the cells are treated with 200 units/ml deoxyribonuclease I (Sigma). In all experiments, $3-5\times 10^5$ cells per liver are obtained.

Isolation of adult liver cells. The two step liver perfusion method is performed to isolate liver cells. After perfusion, the cells are centrifuged for 1 min at 50 g twice to enrich for large parenchymal cells. Cellular viability is >90% as measured by trypan blue exclusion. Flow cytometric analysis. Cells are analyzed on a FACScan (Becton-Dickinson, Mountain View, Calif.) and sorted using a Moflow Flow Cytometer (Cytomation, Fort Collins, Colo.). The cell suspensions from E13 fetal liver are incubated with HBSS, containing 20% goat serum (GIBCO/BRL) and 1% teleostean gelatin (Sigma), on ice to prevent nonspecific antibody binding. After rinsing, the cells are resuspended with FITC-conjugated anti rat $RT1A^{a,b,l}$ antibody B5 (Pharmingen, San Diego, Calif.) and PE-conjugated anti-rat ICAM-1 antibody 1A29 (Pharmingen). In some experiments the cells are stained with biotinylated anti-rat monomorphic MHC class I antibody OX18 (Pharmingen) followed by a second staining with streptavidin-red670 (GIBCO/BRL) for 3 color staining. All stainings are performed with ice-cold $Ca^{++}$ free HBSS containing 10 mM HEPES, 0.8 mM $MgSO_4$, 0.2 mM EGTA, and 0.2% BSA (pH 7.4). The established three hepatic cell lines are trypsinized and fractionated by Percoll density gradient centrifugation to remove feeder cells. The rat hepatoma cell line, FTO-2B, and the rat liver epithelial cell line, WB-F344, as well as adult liver cells are stained to compare with the fetal hepatic cell lines. The cell lines are kind gifts of Dr. R. E. K. Fournier, Fred Hutchinson Cancer Research Center, Seattle, Wash., and Dr. M. S. Tsao, University of North Carolina, Chapel Hill, N.C., respectively. Cells are blocked and stained with FITC-conjugated B5, OX18, PE-conjugated 1A29 or anti FITC-conjugated rat integrin $\beta_1$ antibody Ha2/5 (Pharmingen). FITC-conjugated anti mouse IgG is used for OX18. Cell suspensions of three fetal hepatic cell lines are stained with biotinylated anti-mouse CD98 followed by a second staining with streptavidin-red670 as well as anti-rat moAb to gate out mouse cell populations.

Various antigens are expressed in different relative numbers by cells. In practical usage the level of expression of a particular antigen can be NO expression, a low level of expression, a level of expression that is normal or regular for many antigens, and a high level of expression. In this usage, the term "low" is used interchangeably with a weak or dull. More detailed description of the level of expression can, alternatively, be made, but these four levels suffice for many purposes. It should be clear that measurement of antigen expression by, for example, flow cytometry, provides a continuous range for antigen expression.

CFA for hepatic cell lines, sorted cells, and adult liver cells. The hepatic cell lines are plated in triplicate at 500 cells per 9.6 $cm^2$ on mitomycin C-treated STO feeder layer with the same HDM as used for maintaining each cell line. Before plating, cell are trypsinized and fractionated by Percoll density gradient centrifugation to remove feeder cells. The cultures are incubated for 10 to 14 days with medium changes every other day. Double immunofluorescence staining of alpha-fetoprotein and albumin is then performed. 100 colonies per well are analyzed by the colony morphology, P or F type, and the expression of alpha-fetoprotein and albumin. The colonies are stained using Diff-Quick (Baxter, McGaw Park, Ill.) to count the number of the colonies per well. In the CFA for primary sorted cells and adult liver cells, the plating cell number is changed as described. As another minor modification, the culture period is expanded to between 14 and 17 days, and the concentration of dexamethasone is increased to $10^{-6}$M. All other procedures are performed as above. In the CFA for adult liver cells, small numbers of clumps of liver cells are not eliminated from the cell suspension after the preparation. Therefore, an undefined number of the colonies might be produced from the clumps. For CFA of biliary differentiation on sorted cells, double immunofluorescence staining of albumin and CK19 of the colonies is performed at 5 days each of the culture in the presence or absence of EGF. At day 5 of the cultures, any colony with more than one $CK19^+$ cell is counted as a $CK19^+$ colony. At day 10 and 15, colonies containing multiple clusters of two $CK19^+$ cells or one cluster of more than three $CK19^+$ cells are counted as a $CK19^+$ colony. About 100 colonies per well are counted. Each point represents the mean±SD from triplicate-stained cultures.

6.2. Generation and Characterization of Fetal Rat Hepatic Cell Lines Using Feeders of Mouse Embryonic Cells with a Hormonally Defined Medium.

Simple long-term cultures of rat E15 hepatic cells are attempted to see how long fetal hepatic cells could be maintained and expanded ex vivo to produce progeny. After a gradient density centrifugation to remove hematopoietic mononuclear cells, the fetal liver cells are cultured on culture dishes coated by collagen type IV or laminin and in HDM (see example 6.1). The cells survive well for more than 4 weeks. However, secondary cultures on fresh collagen type IV—or laminin—coated dishes do not permit further expansion. When mitomycin C-treated STO embryonic mouse fibroblast cell lines are used as a feeder layer for the secondary cultures, many aggregates of cells grow. Eventually several stable hepatic cell lines are established from four independent experiments.

Figures 1, 4A:
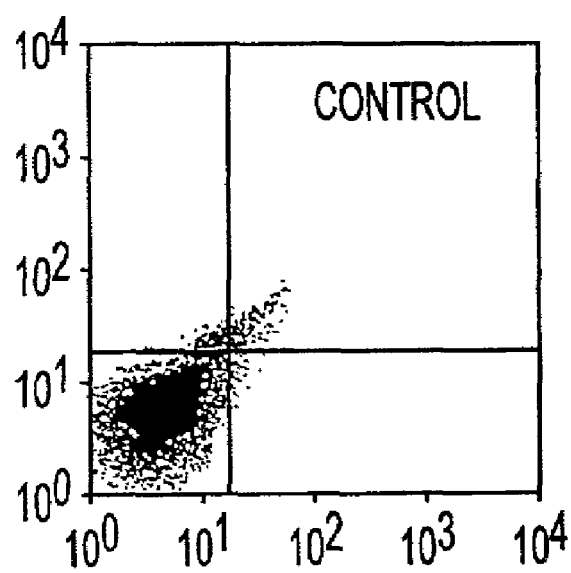
Figures 2, 4A:
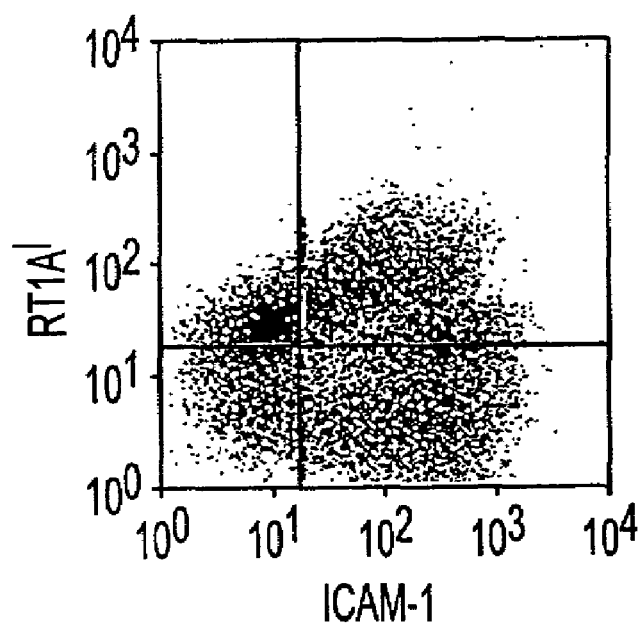
FIG. 2 is an assay of colony formation on fibroblast feeder cells.

Immunohistochemical analysis of alpha-fetoprotein and albumin are performed in the continuous growing cell populations before cloning of the cell lines. Both proteins, alpha-fetoprotein and albumin, are used as the markers to confirm that cell populations originated from the hepatic image. The cell population with a tendency to form piles of cells, is called P-colonies, and has intense expression of alpha-fetoprotein and albumin, while the flattened monolayers, called F-colonies, have diminished expression of alpha-fetoprotein and no albumin. The embyonic mouse fibroblasts, STO, do not show any reactivity to either antibody. For further analysis, three cloned hepatic cell lines from independent experiments are selected by the morphological criteria of either P-type colonies or F-type colonies. Rhe14321 (FIG. 1a) consists mostly of packed small cells, P-type colonies, whereas th1120-3 (FIG. 1c) makes only a flattened monolayer of F-type colonies. Rter6 (FIG. 1b) is an intermediate phenotype of these two. Interestingly, the heterogeneity of rter6 is still observed after three rounds of sequential cloning of the flattened colony. To see the heterogeneity of colonies derived from single cells in rhe13421 and rter6, the cells are cultured on STO fibroblasts for 10 to 14 days at a seeding density of 500 cells per 9.6 cm$^2$ (one well of a 6-well plate). The colonies are then characterized in terms of their morphology and their expression of alpha-fetoprotein and albumin. FIGS. 2a to f shows the results. In the cell lines, rhe14321 (FIG. 2b) and rter6 (FIG. 2c), and in the original cell population prior to cloning (FIG. 2a), almost all P-type colonies strongly express alpha-fetoprotein, whereas F-type colonies of cells do not. Furthermore, the intense expression of both alpha-fetoprotein and albumin is observed only in P-type colonies. The morphological difference in the cloned hepatic cell lines correlate to the percentage of the P-type colony (FIGS. 2b and c). The percentage of P-type colonies in CFA of rter6 and rhe14321 is 33.3% (±8.6% SD) and 65.7% (±4.0% SD), respectively. The total colony number per well is counted to calculate the clonal growth efficiency (colony efficiency). The efficiency of rter6 and rhe14321 is 45.7% (±1.3% SD) and 36.4% (±1.1% SD), respectively. The th1120-3 cells tightly attach to each other along their lateral borders making preparation of single cell suspensions difficult. However, the th 1120-3 cells do not produce piled up clusters.

Figure 1B:
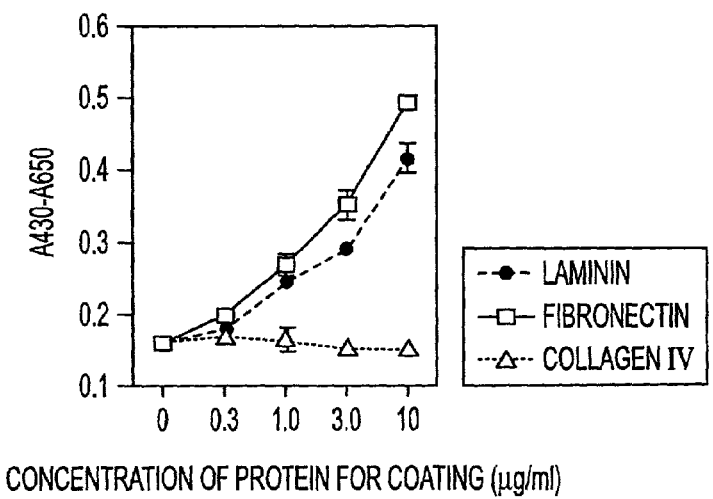
Figure 1C:
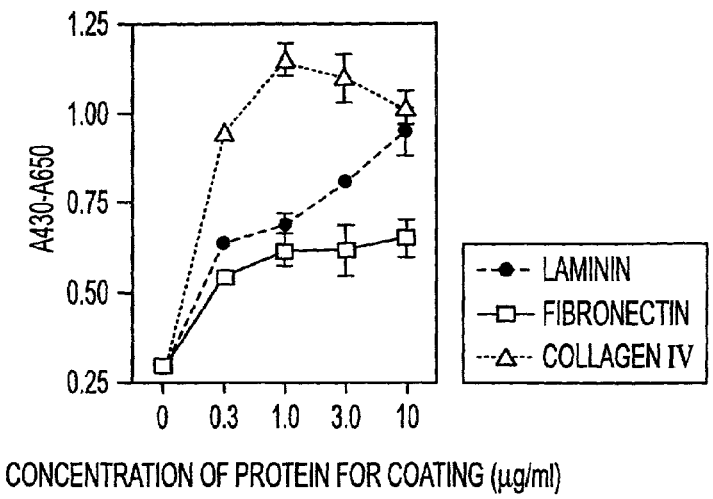

Next, the preferences of each of the cell lines to adhere to specific components of extracellular matrices (ECM) are tested, because the adhesion of mouse liver cells to such ECM proteins as laminin, collagen type IV, and fibronectin, changes in different developmental stages. Whereas collagen type IV is the most effective in the attachment of th1120-3 (FIG. 1c), similar to the findings for the adult liver cells, it works less for rter6 (FIG. 1b) and rhe14321 (FIG. 1a). Laminin is the most effective substratum for adhesion of rhe14321 (FIG. 1a). This preference is similar to that of primary cultures of mouse fetal liver cells. In summary, the conserved expression of alpha-fetoprotein and albumin in P type colonies and preferential adherence to laminin by rhe14321, suggest that the cell populations producing P type colonies are more strictly associated with hepatic progenitor cells.

6.3. Isolation of STO Subclones for the Colony Formation; Assay of Hepatic Progenitors To develop a CFA system to identify bipotent hepatic progenitors with high growth potential, the culture system has to be able to support cell expansion at clonal seeding densities and with conservation of critical original hepatic functions. albumin and alpha-fetoprotein are two of the most significant markers for early hepatic development . The culture conditions optimizing P type colonies should be the best, since P type, but not F type, colonies maintain the expression of alpha-fetoprotein and albumin during clonal expansion. Therefore, STO subclones are compared in their support of P type colonies of rter6. One of the clones, STO5, supports the P type colony formation more than any of the other sublines and more than the parent line (FIG. 2d). The CFA of rhe14321 also confirms that STO5 is a more effective feeder than the parent STO (FIG. 2e).The mouse H1x gene product, expressed in the mesenchymal cells lining digestive tract from E 10.5, is essential for fetal hepatic cell expansion. Although the mRNA expression for the H1x gene is analyzed in all the STO subclones, there is no significant difference in its expression among the subclones (data not shown). Furthermore, the stable transfectants of mouse H1x in STO5 do not result in an improvement in the colony formation assays (FIG. 2f). One clone of the transfectants, however, is used for further experiments, because the transfectant supports a more stable persistence of the original morphology of STOS at relatively high passages.

6.4. Identification of Hepatic Progenitors from E13 Fetal Liver Using the Surface Antigenic Markers and the Colony Forming Assay.

Figure 3A:
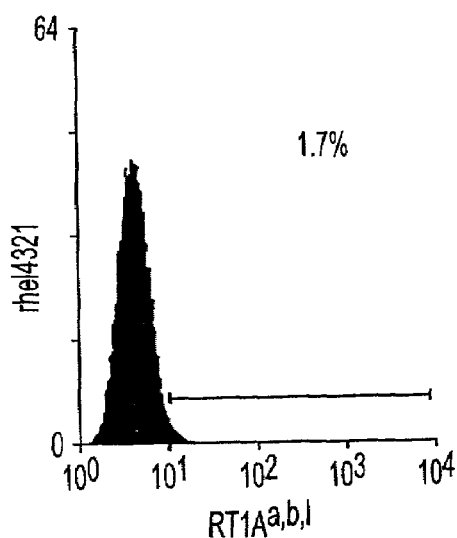
FIG. 3 is an expression of rat cell surface antigens on various hepatic cell lines in adult liver cells.
Figure 3B:
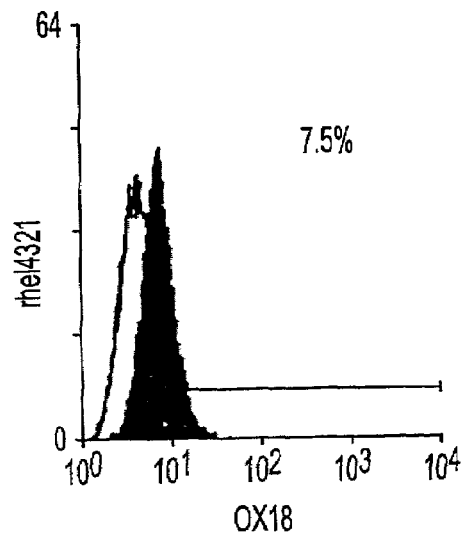
Figure 3C:
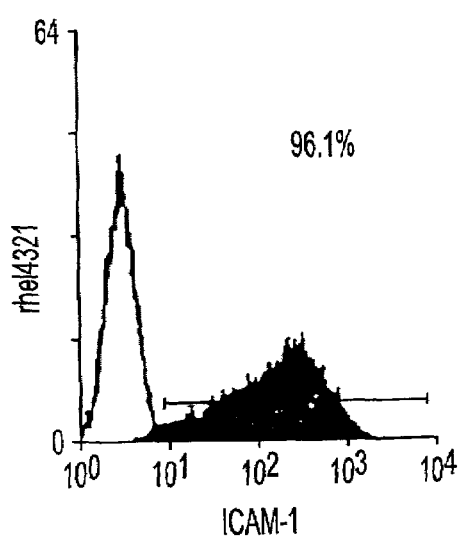
Figure 3D:
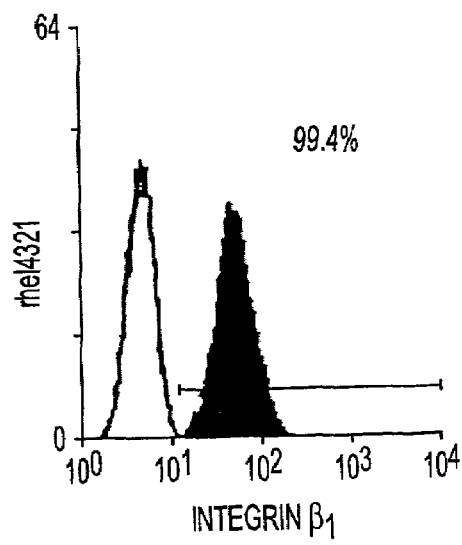
Figure 3E:
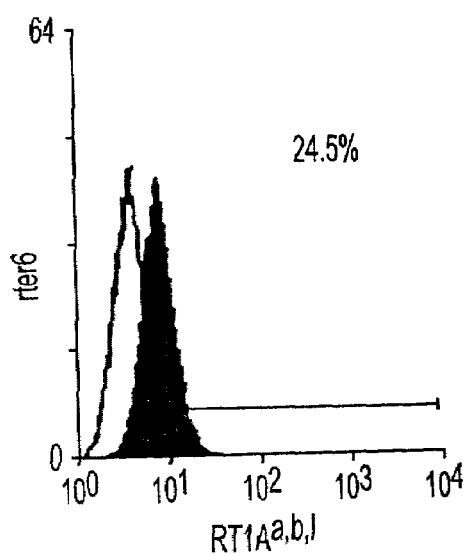
Figure 3F:
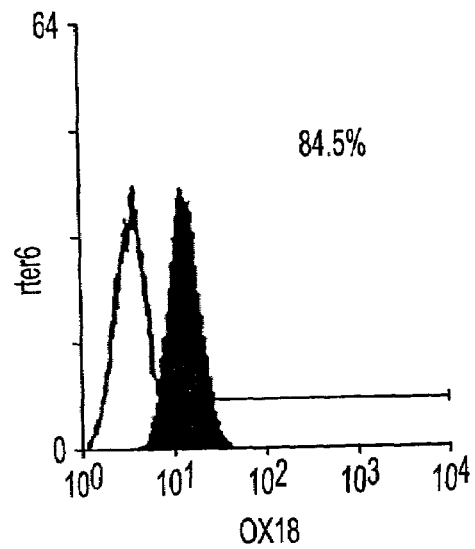
Figure 3G:
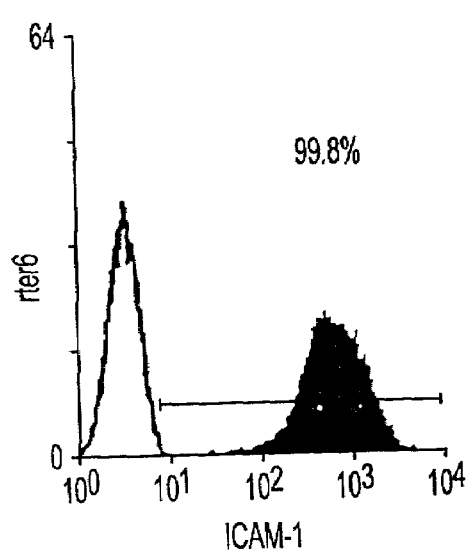
Figure 3H:
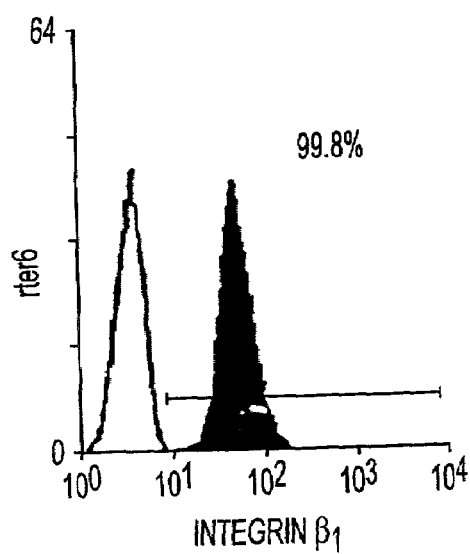
Figure 3I:
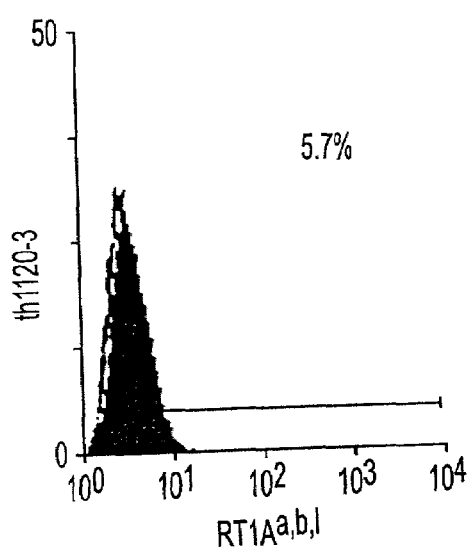
Figure 3J:
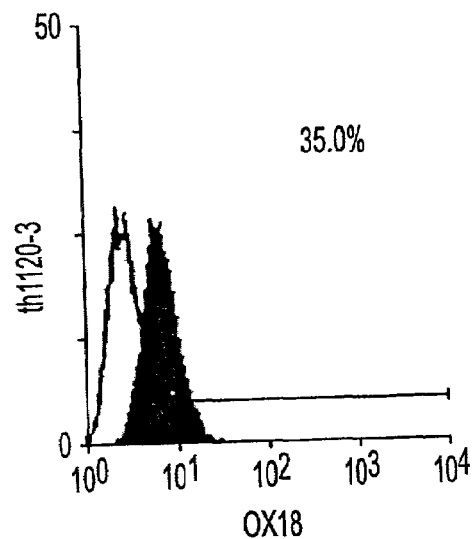
Figure 3K:
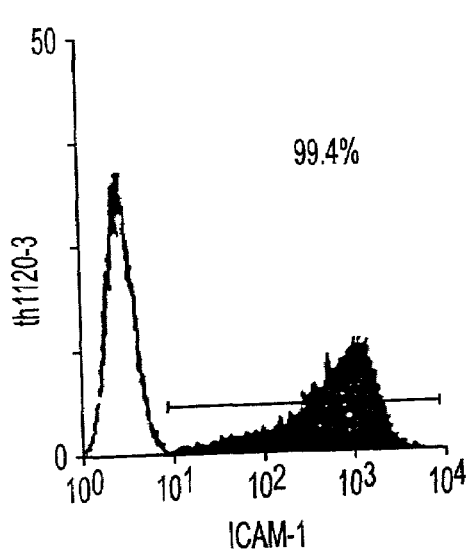
Figure 3L:
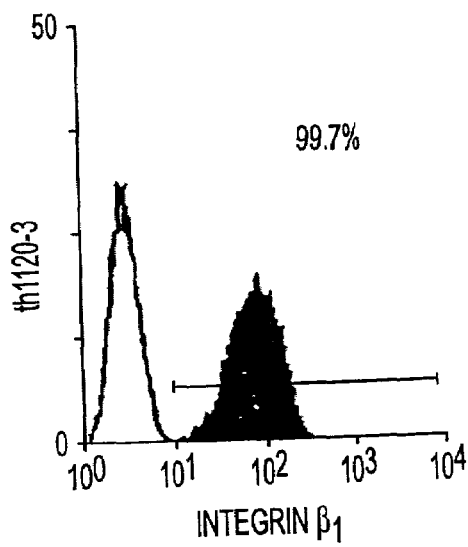
Figure 3M:
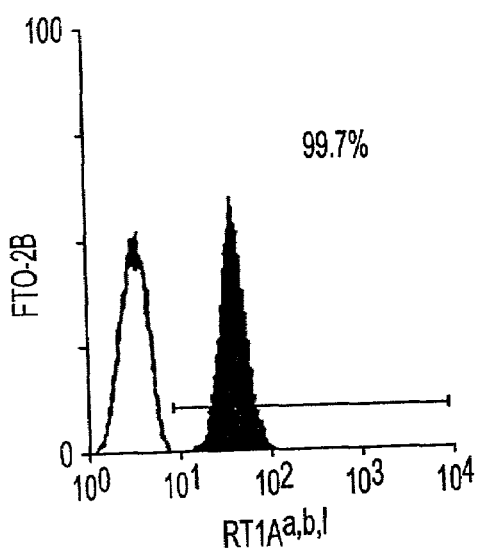
Figure 3N:
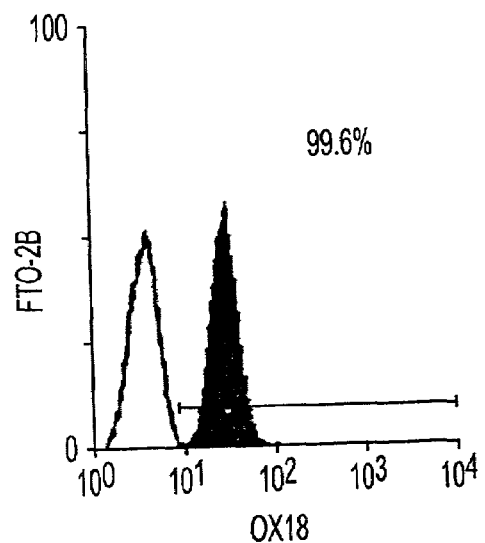
Figure 3O:
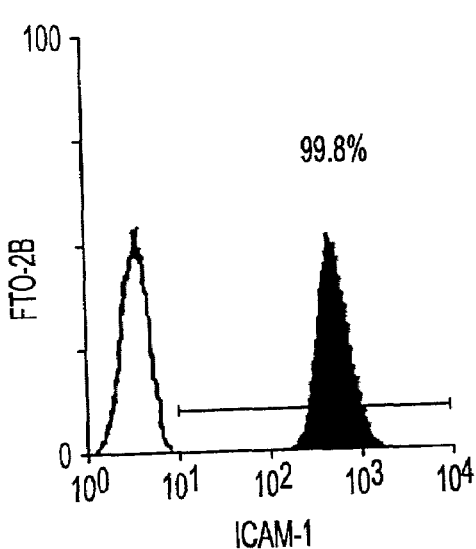
Figure 3P:
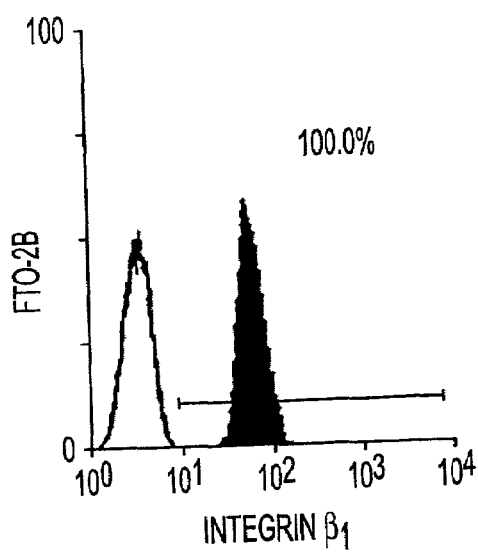
Figure 3Q:
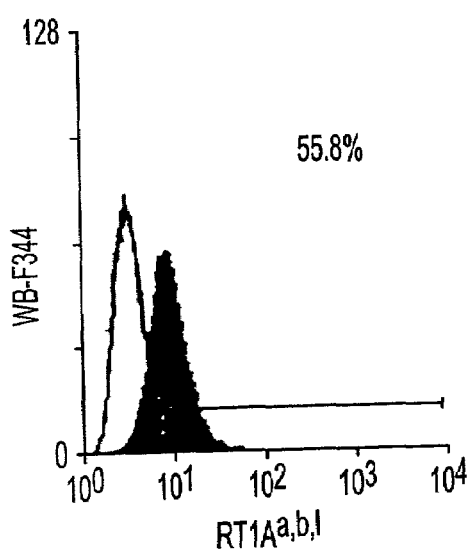
Figure 3R:
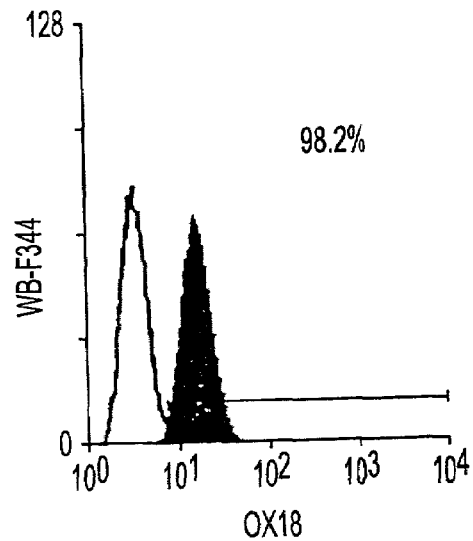
Figure 3S:
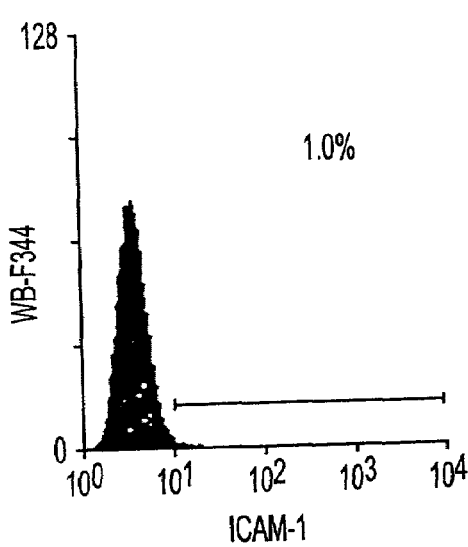
Figure 3T:
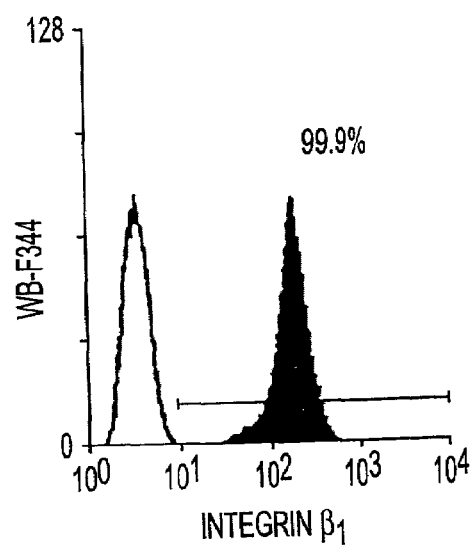
Figure 3U:
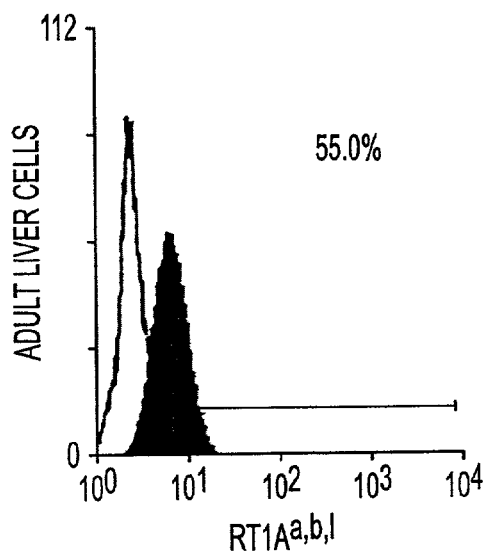
Figure 3V:
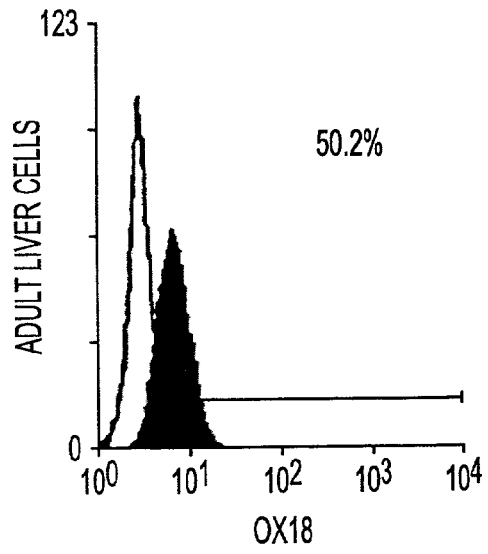
Figure 3W:
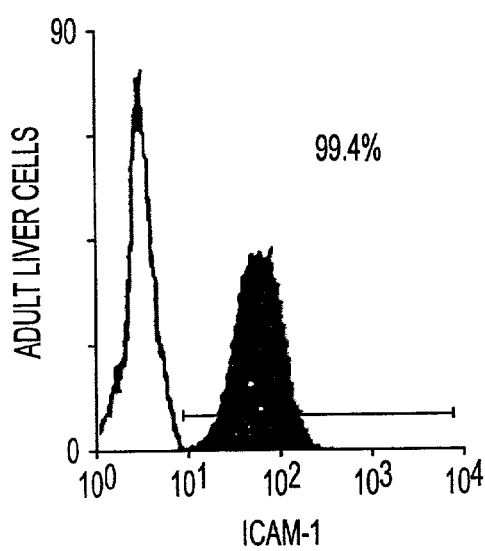
Figure 3X:
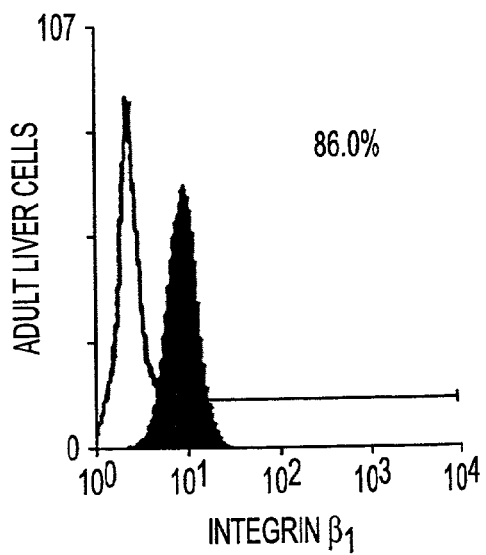
Figures 4, 4C:
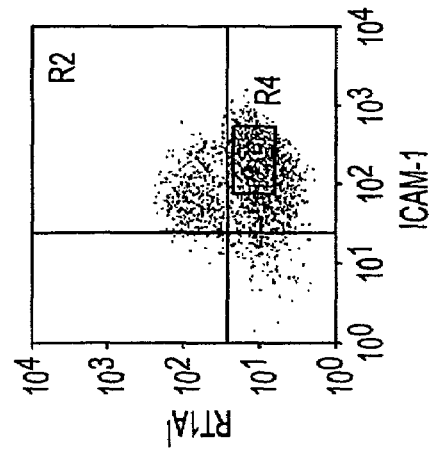
FIG. 4 depicts phenotypic analysis of day 13 fetal rat livers.
Figures 4, 4C, 5:
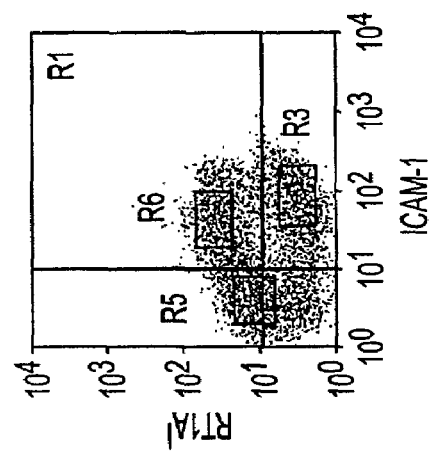
FIG. 5 depicts characterization of hepatic colonies in the absence and presence of EGF.
Figures 2, 4C:
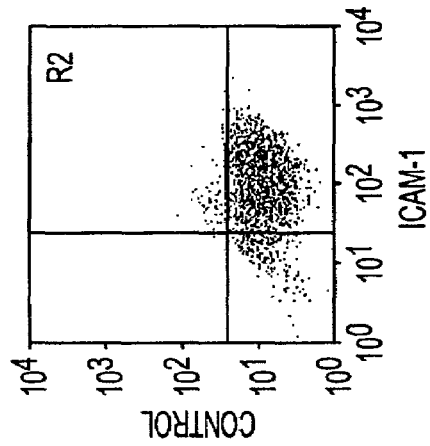
Figures 3, 4C:
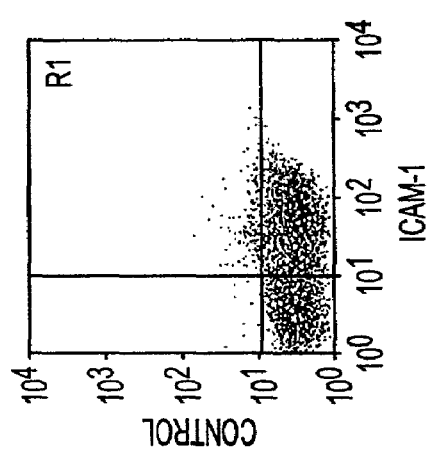
Figures 1, 4C:
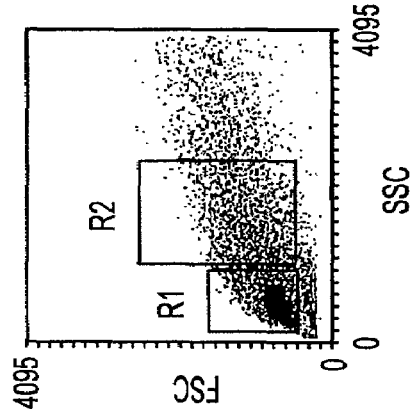
Figures 1, 4D:
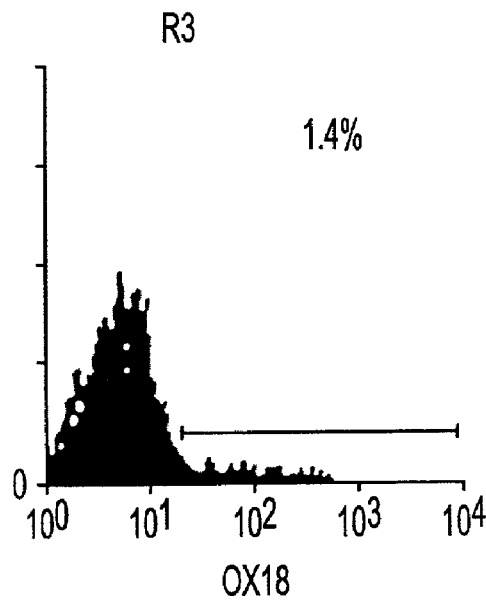
Figures 2, 4D:
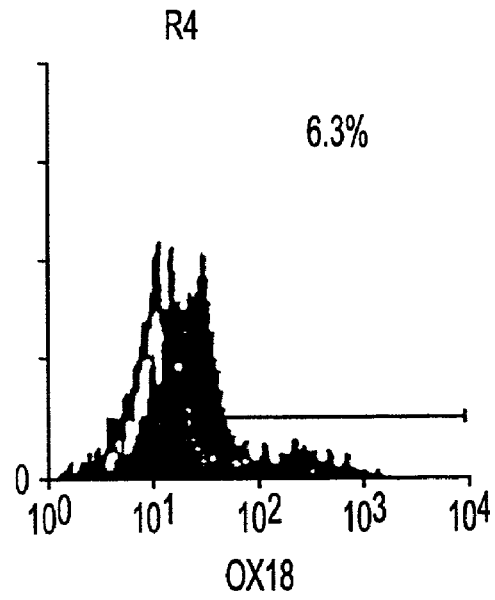
Figures 3, 4D:
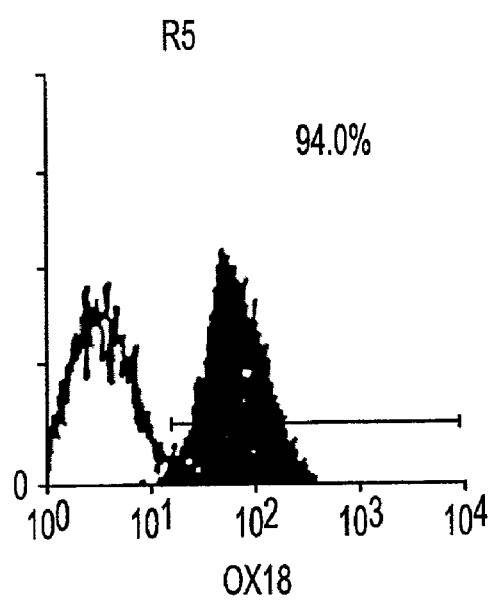
Figures 4, 4D:
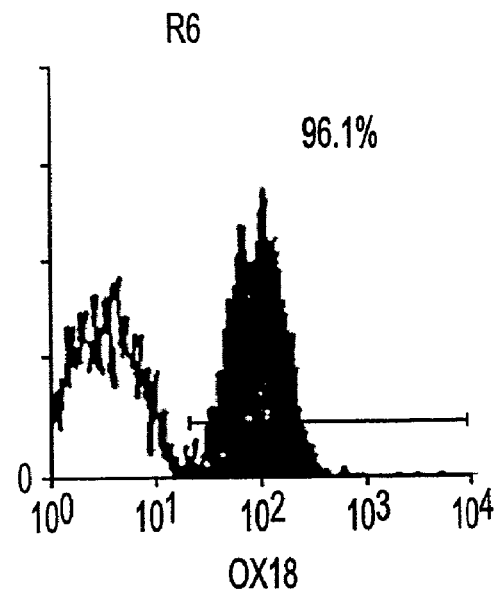

Hepatopoiesis and massive amounts of hematopoiesis co-exist in the fetal liver. So far, the antigenic profile of hematopoietic progenitors has extensively been analyzed, whereas studies of early hepatic progenitors are still in their infancy. The antigenic profile of hepatic cells is analyzed using the three hepatic cell lines established in this study, an adult hepatocarcinoma cell line (FTO-2B), an epithelial cell line from adult rat liver (WB-F344), and freshly isolated adult liver cells. Compared with FTO-2B, WB-F344, and adult liver cells, the pattern of the most immature of the fetal hepatic cell lines, rhe14321, is quite unique in that there is no expression of classical MHC class I ($RT1A^1$) (FIG. 3a-3x). The cell line, th 1120-3 (FIG. 3i-3l), is similar to rhe14321 (FIG. 3a-3d) in the pattern of $RT1A^1$, OX18 (pan-MHC class I), and ICAM-1, whereas rter6 (FIG. 3e-3h) has relatively high expression of $RT1A^1$ and OX18 (FIG. 3). Additionally, another cell line from a different experiment, which has an identical morphology to rhe14321, is also RT1A$^{1-}$, OX18$^{dull}$, and ICAM-1$^{+}$. Integrin b$_1$ expression is similar in all the cell lines, while the pattern of RT1A$^{a,b,1}$ and ICAM-1 is unique among them. The antigenic profile of adult liver cells is RT1A$^{1+}$, OX18$^{+}$, and ICAM-1$^{+}$. Since, in the adult rat, all bone marrow cells except mature erythrocytes strongly express MHC class I molecules, the fetal hepatic population can be separated from the hemopoietic cell populations by MHC class I expression. The cell suspensions from rat E13 livers are stained with anti RT1A$^{1}$ and ICAM-1 antibodies. FIG. 4a shows the 2 color-staining pattern of RT 1 A$^{+}$ and ICAM-1. To determine which fraction contains the hepatic cell population, five fractions are isolated by fluorescent activated cell sorting and then screened by CFA for clonal growth potential. FIG. 4b represents the result of resorting of the five fractions after sorting. The hepatic cell colonies, defined by expression of albumin and alpha-fetoprotein, are distinguishable also morphologically, enabling one to count the number of hepatic colonies per well. The majority of the hepatic colonies are detected in the gate RT1A$^{1dull}$ and ICAM-I$^{+}$ (Table 1, FIG. 4b gate 2), and the frequency of the P type colony is 75.6%±4.9% SD). Gate 1 shows a much lower number of the colonies, and the other fractions contain negligible numbers of cells with colony forming ability. In gates 1 and 2, the expression of both alpha-fetoprotein and albumin is confirmed in all the hepatic colonies. Some of the colonies, derived from cells in gate 2, are larger than others. To investigate the MHC class I expression on the hepatic cells in detail, three color staining of RT1A$^{1}$, ICAM-1, and OX18 with the sidescatter (SSC) as another parameter is used for the cell fractionation. Sidescatter (SSC), a reflection of the granularity of cell, is a useful parameter for separation of hepatic from hematopoietic cells, because fetal hepatic cells contain lipid droplets as early as E11 of gestation (Luzzatto, 1981). FIG. 4c shows that the gate 2 contains the highest number of colony-forming cells. Gating R2 based on the SSC, the population corresponding to the gate 2 clearly shows RT1A$^{1-}$ and OX18$^{dull}$ phenotype (FIG. 4c, 4d). The CFA confirms that R4 harbors more colony-forming cells than gate 2 (Table 1). These results suggest that most of the RT1A$^{1-}$, OX18$^{dull}$, and ICAM-1$^{+}$ population from E13 rat liver are hepatic cells producing alpha-fetoprotein$^{+}$ and albumin$^{+}$ colonies. It is the identical antigenic profile found for rhe14321 cells (FIG. 3).

TABLE 1

The Frequency of hepatic colonies from sorted E13 fetal liver based on the expression of RT1A and ICAM-1.

| Gate | Inoculated cell (per well) | Hepatic colony (per well) | Efficiency of colony formation (%) |
|---|---|---|---|
| 1 | 1000 | 8.7 ± 4.0 | 0.87 |
| 2 | 500 | 136.3 ± 4.6 | 27 |
| 3 | 5000 | 10.0 ± 7.9 | 0.13 |
| 4 | 5000 | 6.3 ± 0.6 | 0.13 |
| 5 | 5000 | 5.0 ± 1.0 | 0.10 |
| R3 | 1000 | 7.0 ± 2.6 | 0.70 |
| R4 | 500 | 269.3 ± 9.8 | 54 |

Colony forming culture on STO5hlx containing indicated cell number from each fraction of E13 of fetal liver. Number of the hepatic colonies was established from triplicate stained cultures (mean±SD). Efficiency of the colony formation express the percentage of cells inoculated to culture that went on to form colonies analyzed after 16 days of the culture.

6.5. Different Growth Requirement of E13 Hepatic Cells and Adult Liver Cells

Figure 6A:
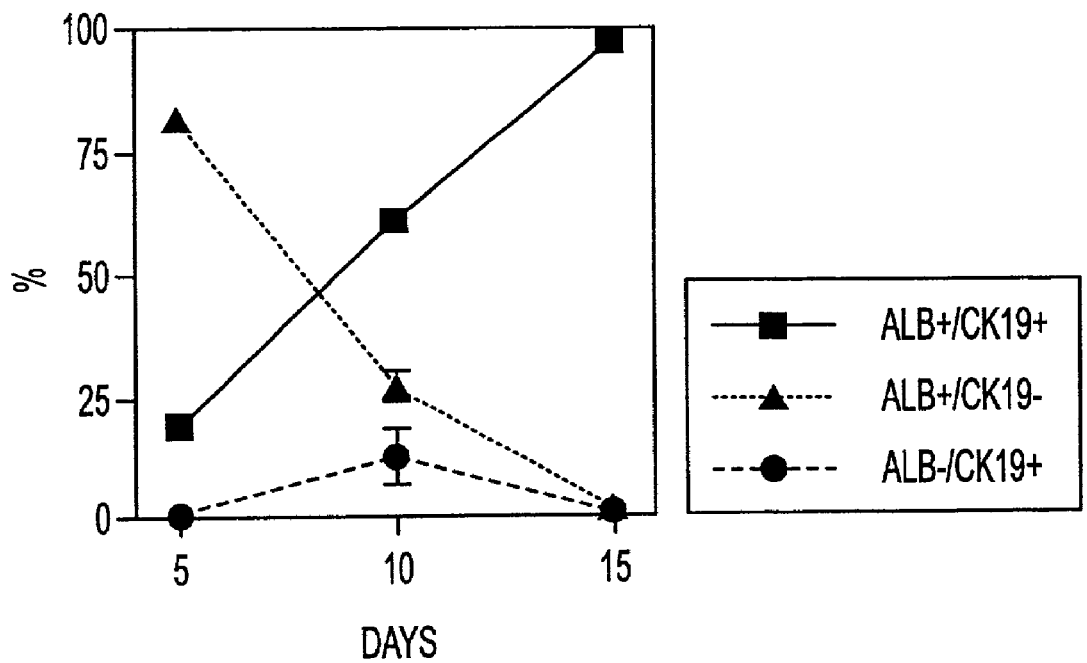
FIG. 6 depicts induction of CK19 expression on RT1A$^{1-}$ hepatic cells.

The growth requirement of the sorted hepatic cells from E13 liver are studied using the defined STO5 feeders and the HDM. EGF has long been known as a potent growth factor for adult liver cells. Therefore, the effects of EGF for colony formation of sorted hepatic cells are investigated. The colony-size of the RT1A$^{1-}$ OX18$^{dull}$ ICAM-1$^{+}$ hepatic cells becomes bigger in the absence of EGF, whereas adult liver cells yielded colonies only in the presence of EGF (FIG. 6c). Furthermore, the morphology of the colonies derived from adult liver cells is the typical F type, whereas all RT1A$^{1-}$ hepatic cells produce P type colonies without EGF. However, the colony efficiency is reduced slightly by the absence of EGF (FIG. 6a). Interestingly, the culture condition in the absence of EGF emphasized the two types of P-colonies, P1 and P2. Although the majority of the colonies is P2 type, at the 12th day of culture, it is difficult to distinguish the two types definitively because some of them do not have the typical morphology like FIG. 6a. These results suggest that fetal hepatic cells and adult liver cells are intrinsically different in their growth requirement as well as in their expression of RT1A$^{1}$ (FIGS. 3 and 4) and colony morphology.

Figure 5A:
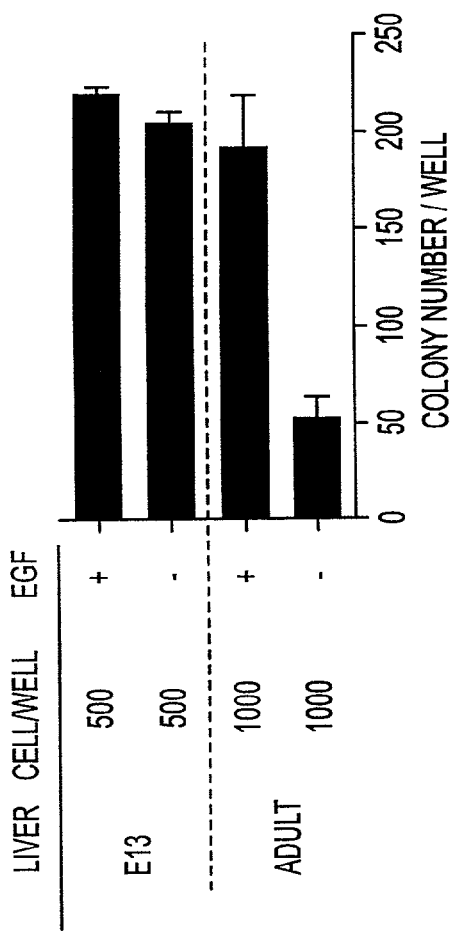
Figure 5D:
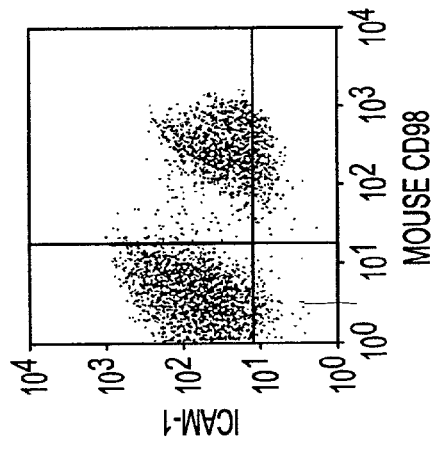
Figure 5C:
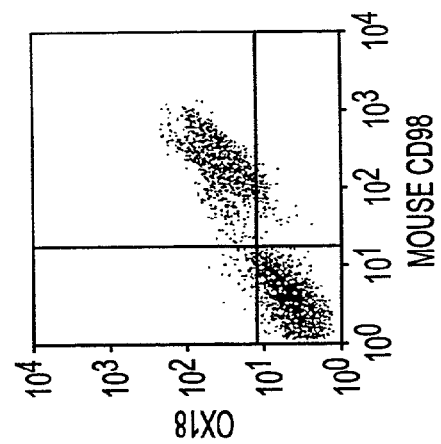
Figure 5B:
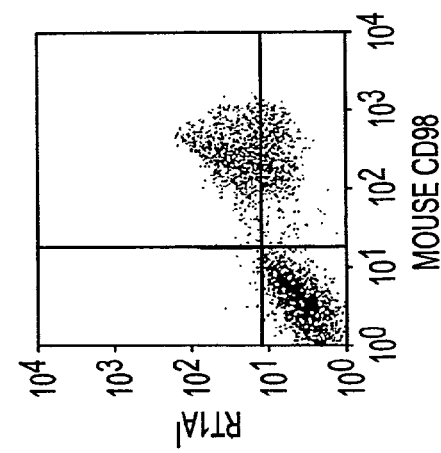

After 3 weeks of culture, when growth seems to reach a maximum, the expression of RT1A$^{1-}$, OX18, and ICAM-1 is assessed. As shown in FIG. 5b-5d, the expression of RT1A$^{1}$ is not induced, while that of OX18 is reduced. The level of ICAM-1 does not change. Furthermore, the average cell number of single colony is calculated from the recovered cell number, the percentage of rat hepatic cells and the colony efficiency. The estimated cell number reaches 3 to 4×10$^{3}$ (Table 2). This indicates that the single cell forming the colonies divided approximately 11-12 times on average under this culture condition.

TABLE 2

Calculation of the cell number in single hepatic colony.

| Inoculated cell number | Seeding density (cell/cm$^2$) | Culture length (day) | Recovered cell number | Percentage of rat cell (%) | Colony efficiency (%) | Average of cell number in single colony |
|---|---|---|---|---|---|---|
| 500 | 18 | 18 | 1.5 × 10$^6$ | 58 | 41 | 4.2 × 10$^3$ |
| 4000 | 51 | 21 | 6.0 × 10$^6$ | 90 | 44 | 3.1 × 10$^3$ |
| 4000 | 51 | 20 | 4.0 × 10$^6$ | 69 | 21 | 3.3 × 10$^3$ |

Sorted cells from R4 in FIG. 4c were cultured on STO5hlx feeder in 60 mm or 100 mm dish. After the period indicated of the culture cell all cells were recovered and the toal cell number counted. The percentage of rat cells is from flow cytometric analysis based on the expression of rat ICAM-1 and mouse CD98. Colony efficiency indicates the percentage of cells inoculated to culture that went on to form colonies. Data from triplicate-stained cultures (mean) was obtained from the experiments run parallel with. Average of cell number in single colony=(Recovered cell number×Percentage of rat cell/100)/Inoculated cell number×Colony efficiency/100).

6.6. Evidence for Bipotentiality in $RT1A^{1-}$ Hepatic Progenitor

Figure 6B:
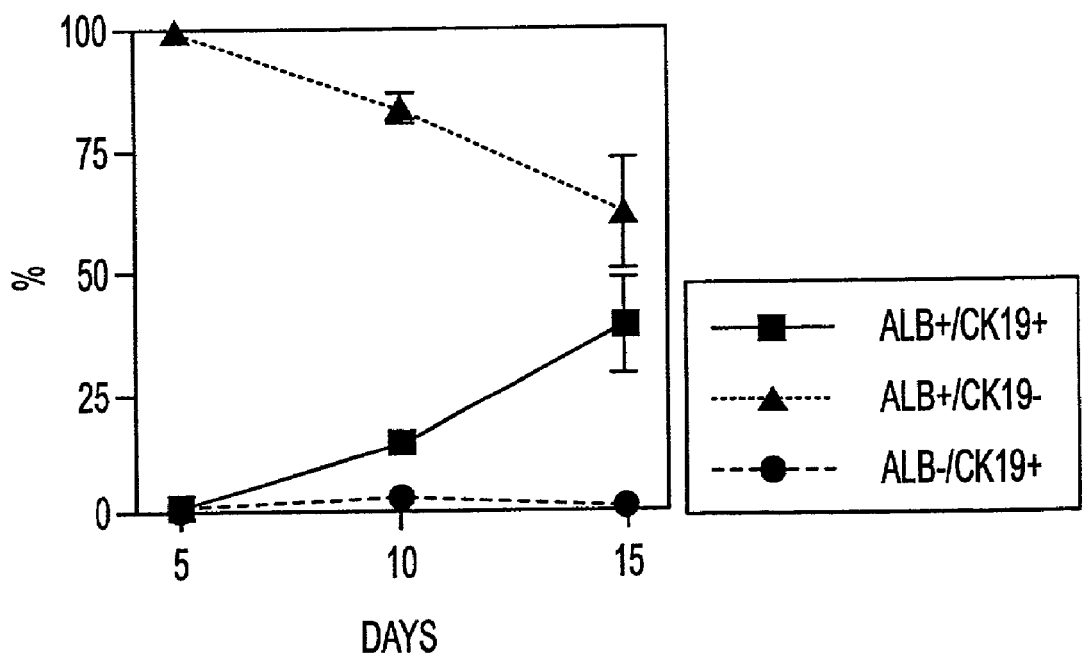
Figure 7:
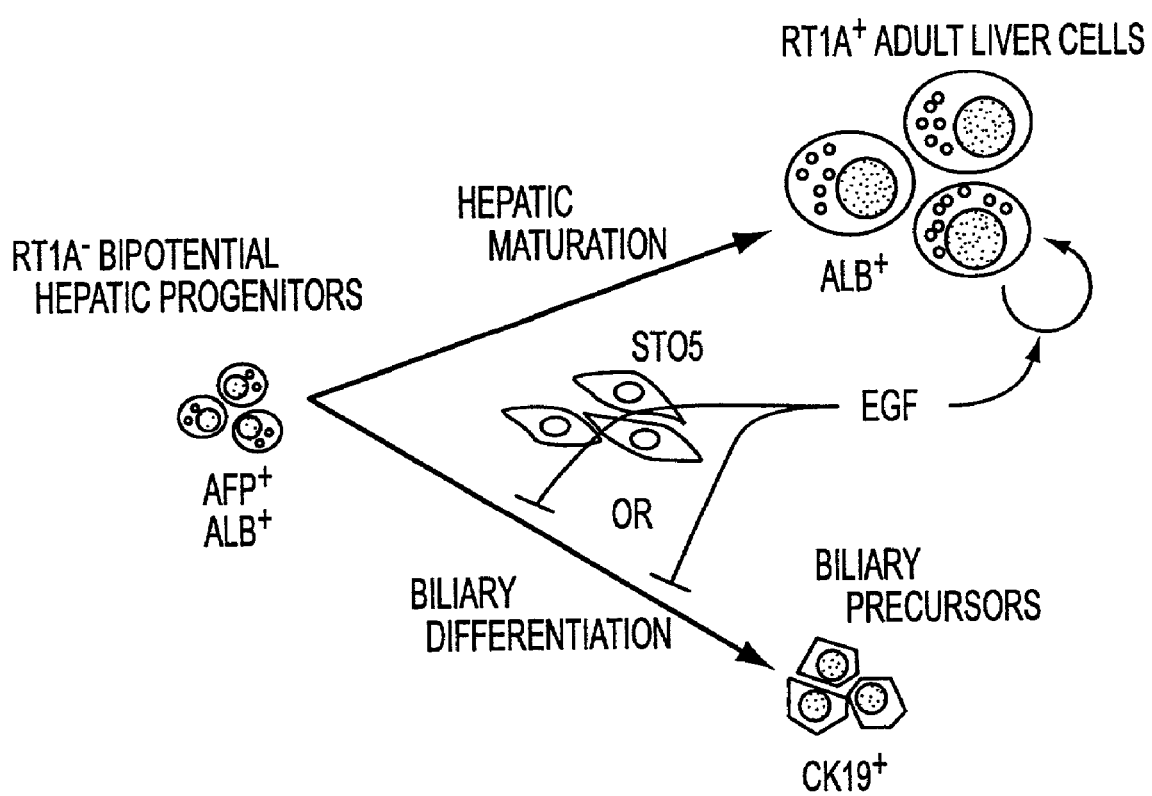
FIG. 7 is a schematic representation of hepatic colony formation on STO5 feeder cells.

At E13 of gestation in the rat, the hepatic cells are thought to have a bipotent precursor giving rise to the mature hepatocyte and bile duct epithelium. However, before the discoveries of the instant invention there has been no direct evidence whether the two fates originated from a single cell or not. To determine whether the $RT1A^{1-}$ $OX18^{dull}$ $ICAM-1^+$ fetal hepatic cells can differentiate to the biliary lineage in this culture system, the colonies are stained by anti-CK19 as a specific marker for biliary epithelial cells. CK19 is expressed in the bile duct epithelial precursors after day 15.5 in the fetal rat liver at which time the expression of albumin disappears in the cells. The sorted $RT1A^{1-}$ $ICAM-1^+$ cells are cultured in the presence or absence of EGF, and their fates are monitored by the expression of CK19 and albumin after 5 days of culture. After the first 5 days, the $CK19^+$ colonies are negligible in the cultures treated with EGF, whereas a few colonies containing $CK19^+$ cells occurred in those in the absence of EGF. Although the intensity of the CK19 expression is fairly weak, the $CK19^+$ cells show reduced albumin expression. At the 10th day of the culture, some colonies apparently express only CK19 or albumin and others have dual positive expression. The pattern of the $CK19^+$ and $albumin^+$ cells in a single colony is reciprocal. The number of dual positive colonies and CK19 single positive colonies still is higher in the absence of EGF (FIG. 6a). In the presence of EGF, many of the colonies consist only of $albumin^+$ cells at the 10th day (FIG. 7b). Eventually, the percentage of dual positive colonies reaches nearly 100% in the absence of EGE at day 15 (FIG. 6a). Altogether, EGF dramatically suppresses the appearance of $CK19^+$ colonies through the culture (FIG. 6b). These results suggest that the $RT1A^{1-}$, $OX18^{dull}$, and $ICAM-1^+$ cells from E13 fetal liver can differentiate towards the biliary lineage and their fate can be influenced by EGF in vitro (FIG. 7).

6.7. Protocol for Isolation and Cloning of Feeder Cells Capable of Sustaining Clonal Growth of Hepatic Stem and Hepatic Progenitor Cells.

Fresh embryonic tissue or frozen tissue (e.g. liver, lung, kidney, muscle, intestine) from pig, beagle, rabbit, mouse or monkey is minced in calcium-free, phosphate-buffered saline (PBS). After rinsing with PBS a couple of times, the cell suspension is incubated with 0.25% trypsin for 10 min at 37° or for 60 min at room temperature with agitating using a magnetic stirrer. The remaining cell chunks are removed by filtering the suspension thorough mesh. The cells are then cultured on tissue culture dishes with a basal medium (e.g. Eagle's MEM) supplemented with serum (e.g. 10% fetal calf serum) and with any of various growth supplements (e.g. 2 mM glutamine, sodium pyruvate, and MEM nonessential amino acids). Plastic substratum and serum supplemented medium are generic conditions that permit expansion of a cell population that is a candidate as support cells ("feeder cells"), most commonly being mesodermally-derived (e.g. stromal cells), and that provide factors supporting the survival, growth and/or functions of another cell type (e.g. progenitor cells). The feeder cells are subcultured with 0.05% trypsin when they become confluent or almost confluent. After several rounds of subculture, expanded cells are prepared as frozen stocks and stored as such until use. An alternative source of feeder cells can be commercially available primary cultures of feeder cells or feeder cell lines. In any case, the following criteria are needed to identify the appropriate feeder cells:

The feeder cells support
1) clonal growth of hepatic progenitors with the phenotypic markers classical MHC class I antigen(s) negative, ICAM-1 positive, and/or nonclassical MHC class I antigen(s) dull positive;
2) clonal growth of progenitors with progeny with the phenotype markers classical MHC class I antigen(s) negative, ICAM-1 positive, nonclassical MHC class I antigen(s) dull positive, alpha-fetoprotein positive, albumin positive or CK19 positive; or
3) inducible differentiation into both hepatic lineage and biliary lineage, required to define bipotent hepatic progenitors.

In the field, classical MHC class I antigen is also known as MHC class Ia antigen. Non-classical MHC class I antigen is also known as MHC class Ib antigen. The MHC antigens have different designations in different species: RT1 in rat, H-2 in mouse, and HLA in humans, for example.

The assays noted above are described below:

A Clonal Growth Condition for Hepatic Progenitors

The hepatic progenitors are plated at 500 cells per 9.6 $cm^2$ on growth-arrested, i.e. cells treated to prevent proliferation, feeder cells. The feeder cells are growth-arrested by treating them with mitomycin C or by irradiating (3000-5000 rads depending upon cell type). The growth-arrested feeder cells and progenitor cells are fed with a serum-free HDM. As an example, HDM for the rodent cells is a 1:1 mixture of Dulbecco's modified Eagle's medium and Ham's F12 with added 10 ng/ml EGF, 5 µg/ml insulin, $10^{-6}$M Dexamethasone, 10 µg/ml iron-saturated transferrin, $4.4 \times 10^{-3}$M nicotinamide, 0.2% bovine serum albumin, $5 \times 10^{-5}$M 2-mercaptoethanol, 7.6 µeq/l free fatty acid, $2 \times 10^{-3}$M glutamine, $1 \times 10^{-6}$M $CuSO_4$, $3 \times 10^{-8}$M $H_2SeO_3$ and antibiotics. The cultures are incubated for 10 to 14 days with medium changes every other day. Double immunofluorescence staining of alpha-fetoprotein, albumin, and/or CK19 is then performed for identifying the fate of the progeny. About 100 colonies are analyzed by the expression of alpha-fetoprotein and albumin. Furthermore the colony morphology, P or F type, could be useful identification of the relevant progeny.

The ideal combination of feeder cells and hepatic progenitors are those that originated from the identical species. Preferably, the feeder cells are from the same tissue and same species as the hepatic progenitors. However, mixing of feeders from one species and progenitors from another is possible. For example, even rodent feeder cells can be used for human hepatic progenitors. Soluble and insoluble factors (that can be species- and/or tissue-specific) help the clonal growth of hepatic stem cells or hepatic progenitors. The source of the factors is:
1) Conditioned medium from the cultured feeder cells of the optimal species and tissue. The feeder cells can be of any cell type, not just stromal cells.
2) When the critical factor(s) are known, one makes a biologically active feeder cell population by introduction into any cells of complementary DNA or mRNA for transcription or translation, respectively, for the synthesis of relevant molecules (signals) derived from optimal feeder cells active for hepatic progenitors.

3) If the critical factor(s) are known, one can also replace the feeder cells altogether by supplementing the medium with those signals, whether they be proteins, peptides, carbohydrates, lipids, glycopeptides, glycoproteins, lipoproteins, glycolipids, or a combination of these constituting the signals derived from optimal feeder cells active for hepatic progenitors.

The above examples have been depicted solely for the purpose of exemplification and are not intended to restrict the scope or embodiments of the invention. Other embodiments not specifically described should be apparent to those of ordinary skill in the art. Such other embodiments are considered to fall, nevertheless, within the scope and spirit of the present invention. Thus, the invention is properly limited solely by the claims that follow.

All patents and publications cited herein are incorporated by reference in their entries.

We claim:

1. A method of propagating primary bipotent hepatic progenitors without inducing their differentiation comprising:
    (a) obtaining liver tissue;
    (b) obtaining a single cell suspension therefrom;
    (c) isolating from the single cell suspension those cells that are MHC class Ia negative, MHC class Ib dull, and positive for ICAM, alpha-fetoprotein, albumin, and cytokeratin-19, to obtain a population of primary bipotent hepatic progenitors having the capacity to differentiate into a hepatocyte or a biliary cell in vitro from the single cell suspension of liver tissue; and
    (d) culturing the primary bipotent hepatic progenitors on a layer comprising embryonic feeder cells in the presence of a culture medium essentially free of both serum and epidermal growth factor (EGF)
    in which the culturing propagates the primary bipotent hepatic progenitors without inducing their differentiation.

2. The method of claim 1 in which the primary bipotent hepatic progenitors are human cells, non-human primate cells, pig cells, dog cells, rabbit cells, rat cells, or mouse cells.

3. The method of claim 2 in which the primary bipotent hepatic progenitors are human cells.

4. The method of claim 1 in which the culture medium comprises a basal medium.

5. The method of claim 4 in which the basal medium includes Dulbecco's modified Eagle's medium and Ham's F12.

6. The method of claim 1 in which the culture medium comprises at least one hormone.

7. The method of claim 6 in which the hormone is insulin.

8. The method of claim 6 in which the culture medium further comprises a glucocorticoid hormone.

9. The method of claim 6 in which the glucocorticoid hormone is dexamethasone.

10. The method of claim 1 in which the culture medium further comprises iron-saturated transferrin.

11. The method of claim 1 in which the culture medium further comprises nicotinamide.

12. The method of claim 1 in which the culture medium further comprises serum albumin.

13. The method of claim 1 in which the culture medium further comprises at least one reducing reagent.

14. The method of claim 13 in which the reducing agent is β-mercaptoethanol.

15. The method of claim 1 in which the culture medium comprises at least one lipid supplement.

16. The method of claim 15 in which the lipid supplement comprises a free fatty acid mixture.

17. The method of claim 15 in which the free fatty acid mixture comprises palmitic acid, palmitoleic acid, stearic acid, oleic acid, linoleic acid, linolenic acid, or combinations thereof.

18. The method of claim 1 in which the culture medium comprises glutamine.

19. The method of claim 1 in which the culture medium further comprises trace elements.

20. The method of claim 19 in which the trace elements comprise $CuSO_4$.

21. The method of claim 19 in which the trace elements comprise $H_2SeO_3$.

22. The method of claim 1 in which the culture medium comprises an antioxidant.

23. The method of claim 22 in which the antioxidant comprises $H_2SeO_3$.

24. The method of claim 1 in which the culture medium further comprises antibiotics.

25. The method of claim 1 in which the feeder cells have an origin which comprises a tissue from at least one vertebrate.

26. The method of claim 25 in which the vertebrate is human, non-human primate, pig, dog, rabbit, rat, or mouse.

27. The method of claim 1 in which the feeder cells comprise stromal cells.

28. The method of claim 1 in which the ICAM is ICAM-1.

29. The method of claim 1 in which the primary bipotent hepatic progenitors grow as piled-up colonies.

30. The method of claim 1 which further comprises cloning the primary bipotent hepatic progenitors.

31. The method of claim 30 in which the cloning utilizes dilution of the cell number, cloning collars, growth in agarose, growth on beads, flow cytometry, or combinations thereof.

32. The method of claim 1 in which the primary bipotent hepatic progenitors undergo at least one mitotic cell division.

33. The method of claim 32 in which the primary bipotent hepatic progenitors undergo at least ten mitotic cell divisions.

34. The method of claim 1 in which the feeder cells are a clone.

35. The method of claim 34 in which the feeder cells are STO cells.

36. The method of claim 1 in which the feeder cells comprise fibroblasts.

* * * * *